(12) United States Patent
Kao

(10) Patent No.: US 9,314,360 B2
(45) Date of Patent: Apr. 19, 2016

(54) BI-DIRECTIONAL STENT DELIVERY SYSTEM

(71) Applicant: VENITI, INC, Saint Louis, MO (US)

(72) Inventor: Stephen Kao, Sunnyvale, CA (US)

(73) Assignee: Veniti, Inc., Fremont, CA (US)

( * ) Notice: Subject to any disclaimer, the term of this patent is extended or adjusted under 35 U.S.C. 154(b) by 0 days.

(21) Appl. No.: 14/487,923

(22) Filed: Sep. 16, 2014

(65) Prior Publication Data

US 2015/0005867 A1    Jan. 1, 2015

Related U.S. Application Data

(62) Division of application No. 12/911,604, filed on Oct. 25, 2010, now Pat. No. 8,864,811.

(60) Provisional application No. 61/352,408, filed on Jun. 8, 2010.

(51) Int. Cl.
*A61F 2/95* (2013.01)
*A61F 2/966* (2013.01)

(52) U.S. Cl.
CPC . *A61F 2/966* (2013.01); *A61F 2/95* (2013.01); *A61F 2002/9517* (2013.01); *A61F 2220/0033* (2013.01)

(58) Field of Classification Search
CPC .... A61F 2/95; A61F 2/962; A61F 2002/9665
See application file for complete search history.

(56) References Cited

U.S. PATENT DOCUMENTS

| | | |
|---|---|---|
| 4,553,545 A | 11/1985 | Maass et al. |
| 4,760,849 A | 8/1988 | Kropf |
| 5,102,417 A | 4/1992 | Palmaz |
| 5,195,984 A | 3/1993 | Schatz |
| 5,201,757 A * | 4/1993 | Heyn et al. ............ 606/198 |
| 5,275,622 A | 1/1994 | Lazarus et al. |

(Continued)

FOREIGN PATENT DOCUMENTS

| | | |
|---|---|---|
| EP | 0 221 570 B1 | 1/1991 |
| EP | 0 335 341 B1 | 3/1992 |

(Continued)

OTHER PUBLICATIONS

U.S. Office Action dated Aug. 6, 2014 from U.S. Appl. No. 13/156,327.

(Continued)

*Primary Examiner* — Diane Yabut
(74) *Attorney, Agent, or Firm* — Oliff PLC

(57) ABSTRACT

A bi-directional stent delivery system includes an inner elongate shaft, a radially expandable prosthesis disposed over the inner elongate shaft, an outer elongate shaft, and a shuttle sheath disposed over the radially expandable prosthesis. The distal portion of the inner shaft is releasably coupled to the distal portion of the shuttle sheath, and the distal portion of the outer shaft is releasably coupled the proximal portion of the shuttle sheath. Distal advancement of the inner shaft advances the shuttle sheath distally when the outer shaft is uncoupled from the shuttle sheath, thereby allowing the prosthesis to radially expand from a proximal end to a distal end. Proximal retraction of the outer shaft retracts the shuttle sheath proximally when the inner shaft is uncoupled from the shuttle sheath, thereby allowing the prosthesis to radially expand from a distal end to a proximal end thereof.

31 Claims, 17 Drawing Sheets

(56) References Cited

U.S. PATENT DOCUMENTS

| | | | |
|---|---|---|---|
| 5,292,321 A | 3/1994 | Lee | |
| 5,443,500 A | 8/1995 | Sigwart | |
| 5,449,373 A | 9/1995 | Pinchasik et al. | |
| 5,449,382 A | 9/1995 | Dayton | |
| 5,451,233 A | 9/1995 | Yock | |
| 5,545,210 A | 8/1996 | Hess et al. | |
| 5,591,197 A | 1/1997 | Orth et al. | |
| 5,603,698 A | 2/1997 | Roberts et al. | |
| 5,649,949 A | 7/1997 | Wallace et al. | |
| 5,669,932 A | 9/1997 | Fischell et al. | |
| 5,693,085 A | 12/1997 | Buirge et al. | |
| 5,733,303 A | 3/1998 | Israel et al. | |
| 5,743,873 A | 4/1998 | Cai et al. | |
| 5,755,776 A | 5/1998 | Al Saadon | |
| 5,755,781 A | 5/1998 | Jayaraman | |
| 5,776,142 A | 7/1998 | Gunderson | |
| 5,792,165 A | 8/1998 | Klieman et al. | |
| 5,810,872 A | 9/1998 | Kanesaka et al. | |
| 5,836,964 A | 11/1998 | Richter et al. | |
| 5,873,907 A | 2/1999 | Frantzen | |
| 5,893,887 A | 4/1999 | Jayaraman | |
| 5,902,333 A | 5/1999 | Roberts et al. | |
| 5,907,893 A | 6/1999 | Zadno Azizi et al. | |
| 5,919,204 A * | 7/1999 | Lukic et al. | 606/198 |
| 5,925,061 A | 7/1999 | Ogi et al. | |
| 5,954,743 A | 9/1999 | Jang | |
| 6,042,597 A | 3/2000 | Kveen et al. | |
| 6,129,755 A | 10/2000 | Mathis et al. | |
| 6,193,745 B1 | 2/2001 | Fogarty et al. | |
| 6,241,757 B1 | 6/2001 | An et al. | |
| 6,254,612 B1 | 7/2001 | Hieshima | |
| 6,261,318 B1 | 7/2001 | Lee et al. | |
| 6,264,690 B1 | 7/2001 | Von Oepen | |
| 6,352,552 B1 | 3/2002 | Levinson et al. | |
| 6,468,299 B2 | 10/2002 | Stack et al. | |
| 6,562,064 B1 | 5/2003 | deBeer | |
| 6,579,308 B1 | 6/2003 | Jansen et al. | |
| 6,585,758 B1 | 7/2003 | Chouinard et al. | |
| 6,599,314 B2 | 7/2003 | Mathis | |
| 6,602,281 B1 | 8/2003 | Klein | |
| 6,605,110 B2 | 8/2003 | Harrison | |
| 6,656,220 B1 | 12/2003 | Gomez et al. | |
| 6,682,554 B2 | 1/2004 | Oepen et al. | |
| 6,699,278 B2 | 3/2004 | Fischell et al. | |
| 6,716,238 B2 | 4/2004 | Elliott | |
| 6,749,629 B1 | 6/2004 | Hong et al. | |
| 6,761,731 B2 | 7/2004 | Majercak | |
| 6,776,793 B2 | 8/2004 | Brown et al. | |
| 6,799,357 B2 | 10/2004 | Webb et al. | |
| 6,849,084 B2 * | 2/2005 | Rabkin et al. | 623/1.12 |
| 6,878,162 B2 | 4/2005 | Bales et al. | |
| 6,929,660 B1 | 8/2005 | Ainsworth et al. | |
| 6,955,688 B2 | 10/2005 | Wilson et al. | |
| 7,018,401 B1 * | 3/2006 | Hyodoh et al. | 623/1.12 |
| 7,122,049 B2 | 10/2006 | Banas et al. | |
| 7,131,993 B2 | 11/2006 | Gregorich | |
| 7,137,993 B2 | 11/2006 | Acosta et al. | |
| 7,163,553 B2 | 1/2007 | Limon | |
| 7,252,679 B2 | 8/2007 | Fischell et al. | |
| 7,344,560 B2 | 3/2008 | Gregorich et al. | |
| 7,520,890 B2 | 4/2009 | Phillips | |
| 7,556,644 B2 | 7/2009 | Burpee | |
| 7,594,927 B2 | 9/2009 | Majercak et al. | |
| 7,611,531 B2 | 11/2009 | Calisse | |
| 7,722,661 B2 | 5/2010 | Lenz et al. | |
| 8,317,859 B2 * | 11/2012 | Snow et al. | 623/6.12 |
| 8,337,546 B2 | 12/2012 | Bruszewski | |
| 2001/0044650 A1 | 11/2001 | Simso et al. | |
| 2002/0082682 A1 | 6/2002 | Barclay et al. | |
| 2002/0120323 A1 | 8/2002 | Thompson et al. | |
| 2002/0188341 A1 | 12/2002 | Elliott | |
| 2003/0040771 A1 | 2/2003 | Hyodoh et al. | |
| 2003/0097172 A1 | 5/2003 | Shalev et al. | |
| 2003/0114920 A1 | 6/2003 | Caro et al. | |
| 2003/0130726 A1 | 7/2003 | Thorpe et al. | |
| 2003/0195609 A1 | 10/2003 | Berenstein et al. | |
| 2004/0006381 A1 | 1/2004 | Sequin et al. | |
| 2004/0088044 A1 | 5/2004 | Brown et al. | |
| 2004/0147997 A1 * | 7/2004 | Gittings | 623/1.11 |
| 2004/0158247 A1 | 8/2004 | Sitiso et al. | |
| 2004/0158312 A1 | 8/2004 | Chouinard et al. | |
| 2004/0167609 A1 | 8/2004 | Majercak | |
| 2004/0186556 A1 | 9/2004 | Hogendijk et al. | |
| 2004/0186560 A1 | 9/2004 | Alt | |
| 2004/0204752 A1 | 10/2004 | Ehr et al. | |
| 2004/0220585 A1 | 11/2004 | Nikolchec | |
| 2005/0015136 A1 | 1/2005 | Ikeuchi et al. | |
| 2005/0055080 A1 | 3/2005 | Lstephanous et al. | |
| 2005/0107863 A1 | 5/2005 | Brown | |
| 2005/0131516 A1 | 6/2005 | Greenhalgh | |
| 2005/0288764 A1 * | 12/2005 | Snow et al. | 623/1.11 |
| 2006/0020322 A1 | 1/2006 | Leynov et al. | |
| 2006/0074474 A1 * | 4/2006 | Theron | 623/1.11 |
| 2006/0106452 A1 | 5/2006 | Niermann | |
| 2006/0116751 A1 | 6/2006 | Bayle et al. | |
| 2006/0142849 A1 | 6/2006 | Killion et al. | |
| 2006/0247759 A1 | 11/2006 | Burpee et al. | |
| 2007/0055348 A1 | 3/2007 | Pryor | |
| 2007/0129786 A1 | 6/2007 | Beach et al. | |
| 2007/0185563 A1 | 8/2007 | Zarbatany et al. | |
| 2007/0219618 A1 | 9/2007 | Cully et al. | |
| 2007/0255387 A1 | 11/2007 | Kramer et al. | |
| 2008/0103584 A1 | 5/2008 | Su et al. | |
| 2008/0109068 A1 | 5/2008 | Fischell et al. | |
| 2008/0125849 A1 | 5/2008 | Burpee et al. | |
| 2008/0208319 A1 | 8/2008 | Rabkin et al. | |
| 2008/0215129 A1 | 9/2008 | Venturelli et al. | |
| 2008/0294230 A1 | 11/2008 | Parker | |
| 2008/0294240 A1 | 11/2008 | Casey | |
| 2008/0306581 A1 | 12/2008 | Berglund et al. | |
| 2009/0036976 A1 | 2/2009 | Beach et al. | |
| 2009/0118810 A1 | 5/2009 | Klein et al. | |
| 2009/0163989 A1 | 6/2009 | Contilliano et al. | |
| 2009/0182407 A1 | 7/2009 | Leanna et al. | |
| 2009/0210049 A1 | 8/2009 | Thielen et al. | |
| 2009/0264978 A1 | 10/2009 | Dieck et al. | |
| 2010/0004730 A1 * | 1/2010 | Benjamin et al. | 623/1.11 |
| 2010/0023106 A1 | 1/2010 | Meyer et al. | |
| 2010/0057187 A1 | 3/2010 | Caldarise et al. | |
| 2010/0137973 A1 | 6/2010 | Sutermeister et al. | |
| 2010/0294287 A1 | 11/2010 | Raju et al. | |
| 2011/0106237 A1 | 5/2011 | Bonsignore et al. | |
| 2011/0230957 A1 | 9/2011 | Bonsignore et al. | |
| 2011/0307049 A1 | 12/2011 | Kao | |
| 2012/0078341 A1 | 3/2012 | Kao | |
| 2012/0078344 A1 | 3/2012 | Kao | |

FOREIGN PATENT DOCUMENTS

| | | |
|---|---|---|
| EP | 1 304 091 A2 | 4/2003 |
| JP | 2008-504078 A | 2/2008 |
| WO | WO 98/38945 | 9/1998 |
| WO | WO 00/16718 A1 | 3/2000 |
| WO | WO 0057813 | 10/2000 |
| WO | WO 03051425 A2 | 6/2003 |
| WO | 2006/005082 A2 | 1/2006 |
| WO | 2007/098232 A2 | 8/2007 |
| WO | WO 2007092276 A2 | 8/2007 |

OTHER PUBLICATIONS

Boston Scientific Corporation, Ultraflex Tracheobronchial Stent System, copyright 2007; retrieved from the Internet: http://www.bostonscientific.com/templatedata/imports/collateral/PulmonaryEndoscopy/prospec_ultrfxtb_01_us.pdf, 2 pages total.

U.S. Appl. No. 12/903,056, filed Oct. 12, 2010; first named Inventor: Seshadri Raju.

Raju et al.; U.S. Appl. No. 11/944,094 entitled "Venous Stent," filed Nov. 21, 2007.

(56) References Cited

OTHER PUBLICATIONS

Raju et al.; U.S. Appl. No. 12/903,056 entitled "Venous Stent, "filed Oct. 22, 2009.
Duerig et al.; An overview of superelesteic stent design; Min Invas Ther & Allied Technol; vol. 9(3/4); pp. 235-246; (year of publication is sufficiently earlier than the effective U.S. filed and any foreign priority date) 2000.
Malve et at.; FSI analysis of the coughing mechanism in a human trachea; Annals of Biomedical Engineering; vol. 38; No. 4; pp. 1556-1565; Apr. 2010.
Feb. 13, 2015 Office Action issued in Chinese Patent Application No. 201180037918.8.
Mar. 24, 2015 Office Action issued in Japanese Patent Application No. 2013-514350.

* cited by examiner

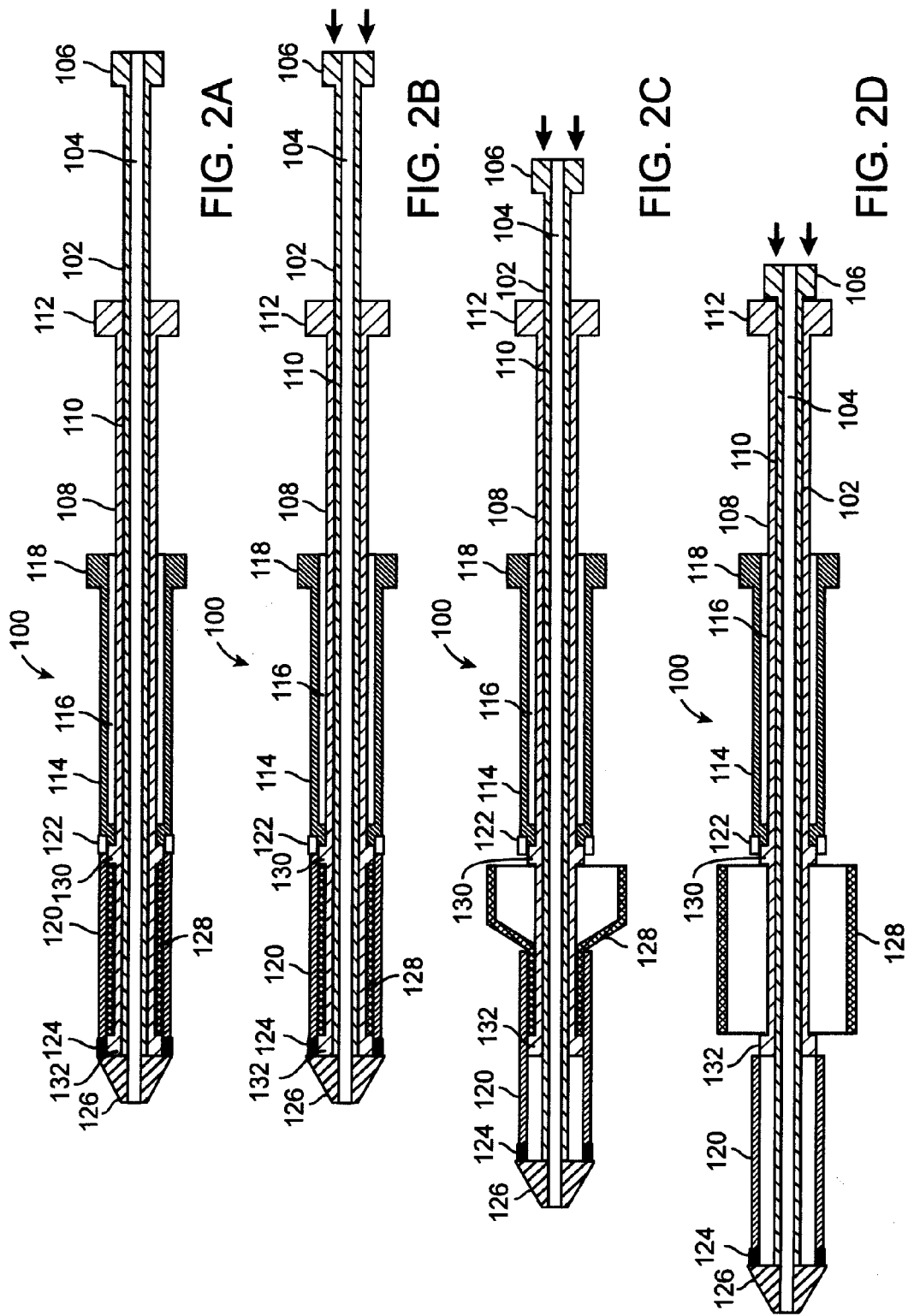

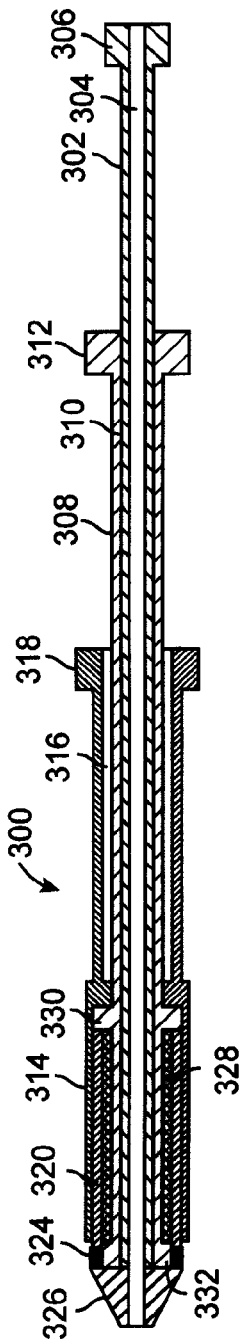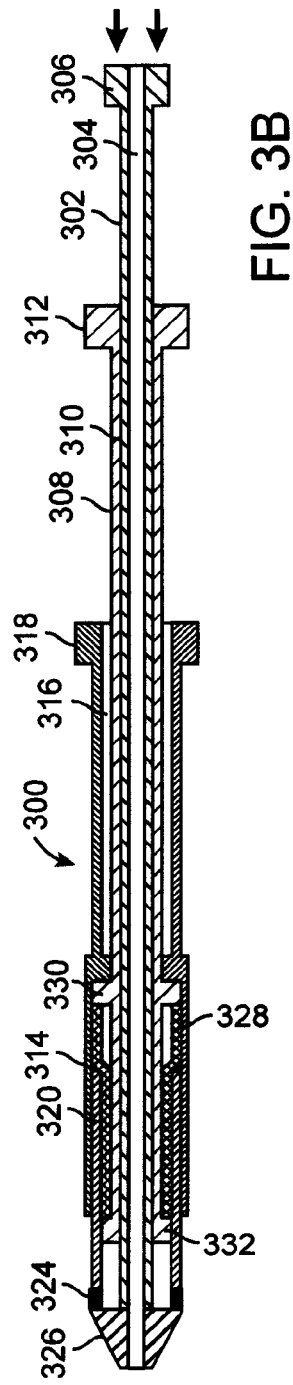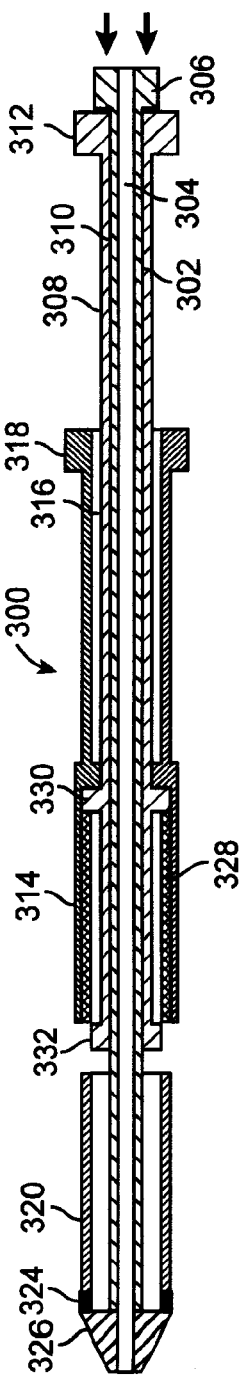
FIG. 3A
FIG. 3B
FIG. 3C

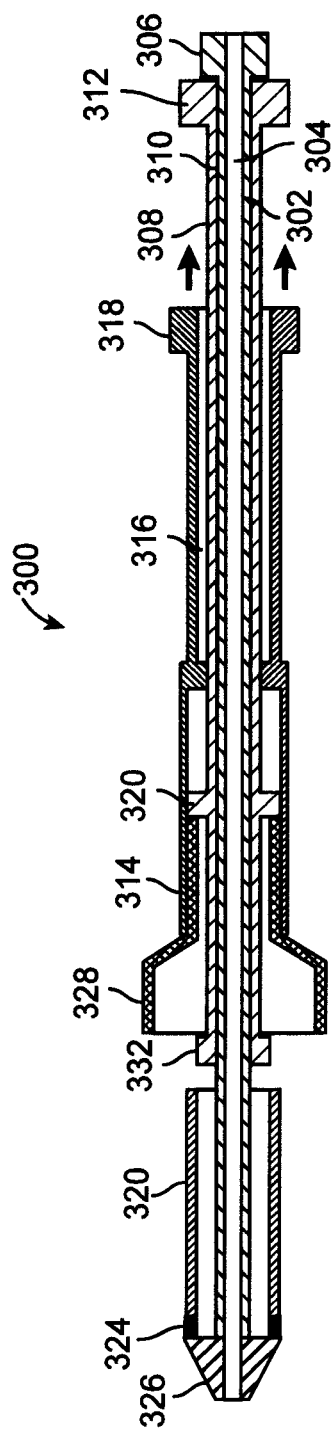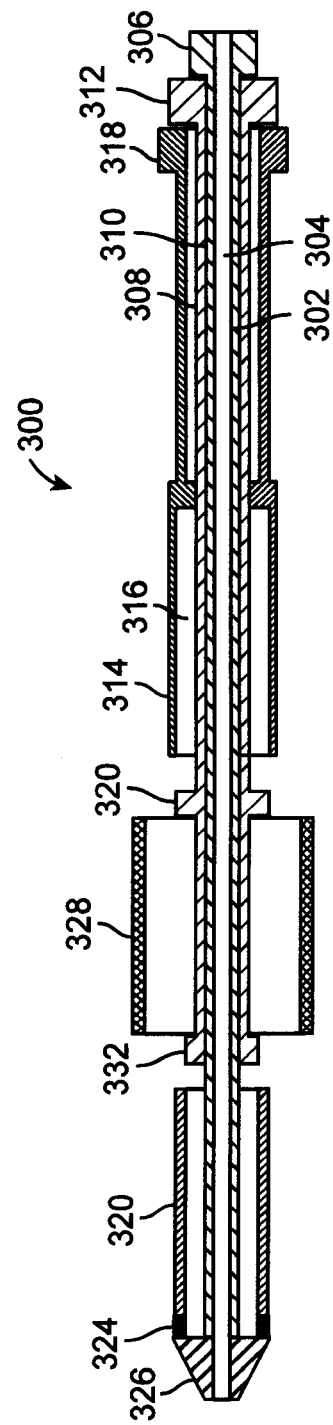
FIG. 3D
FIG. 3E

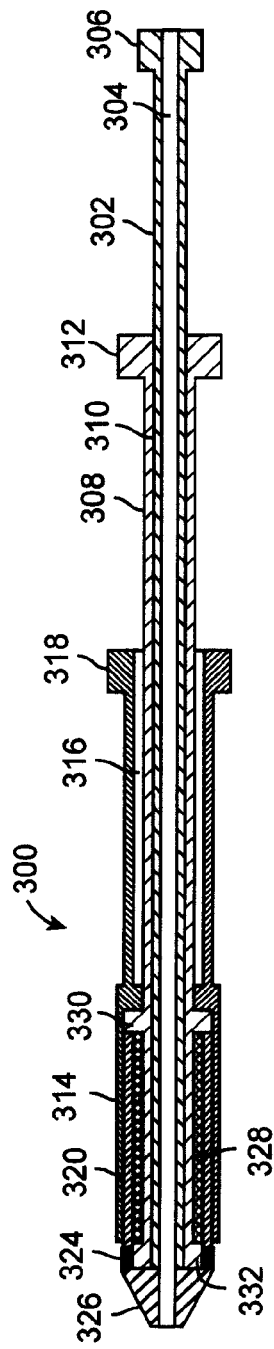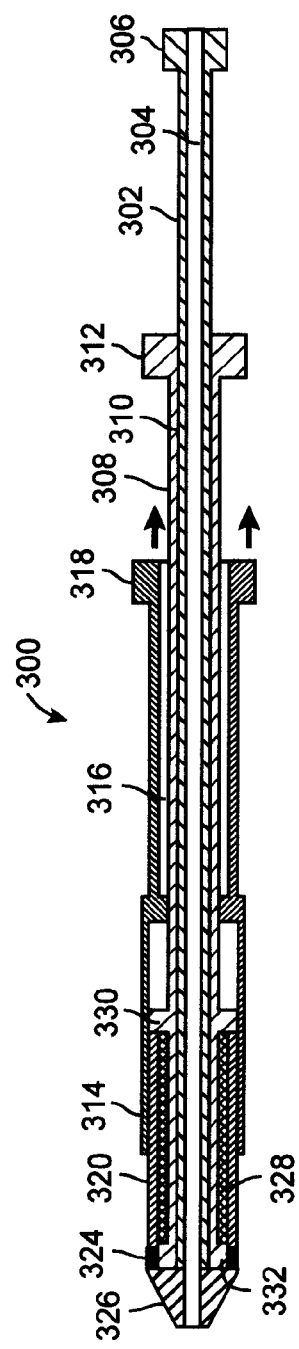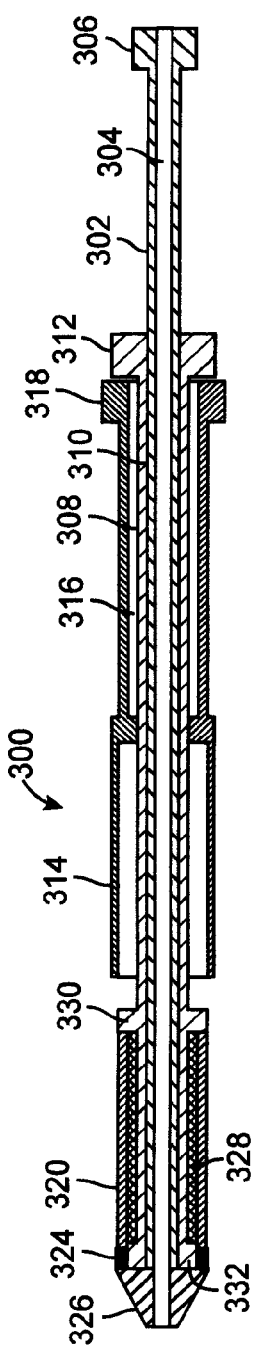

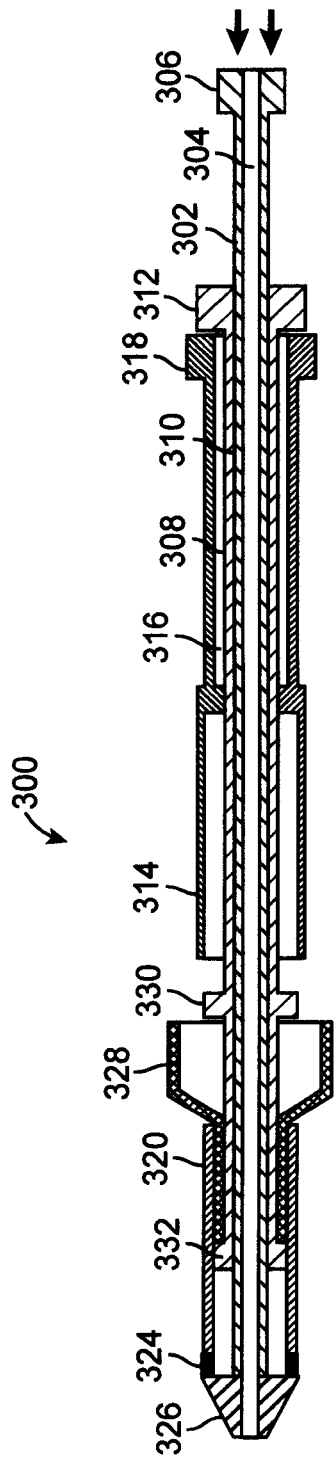
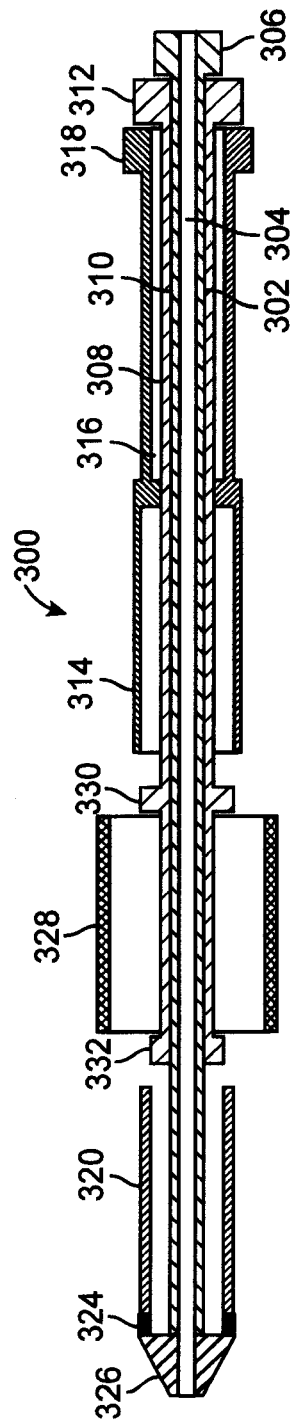
FIG. 4D
FIG. 4E

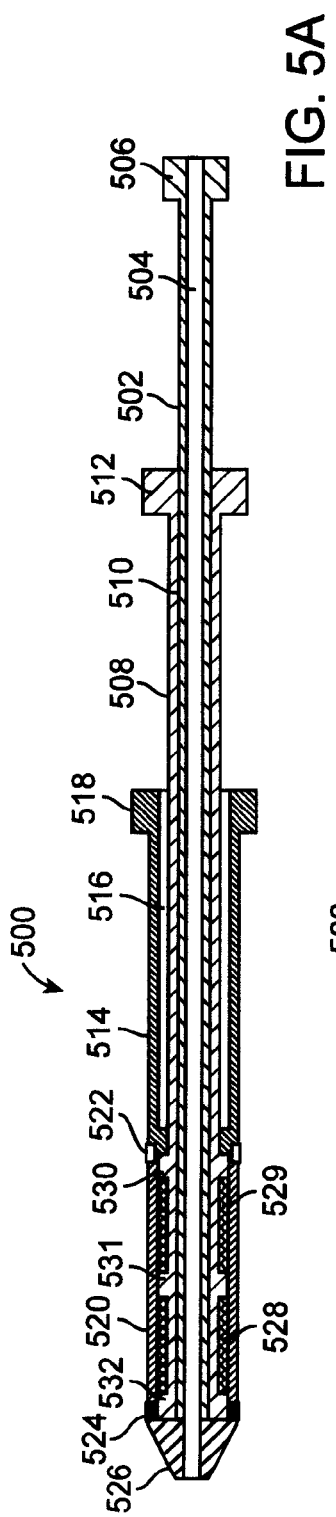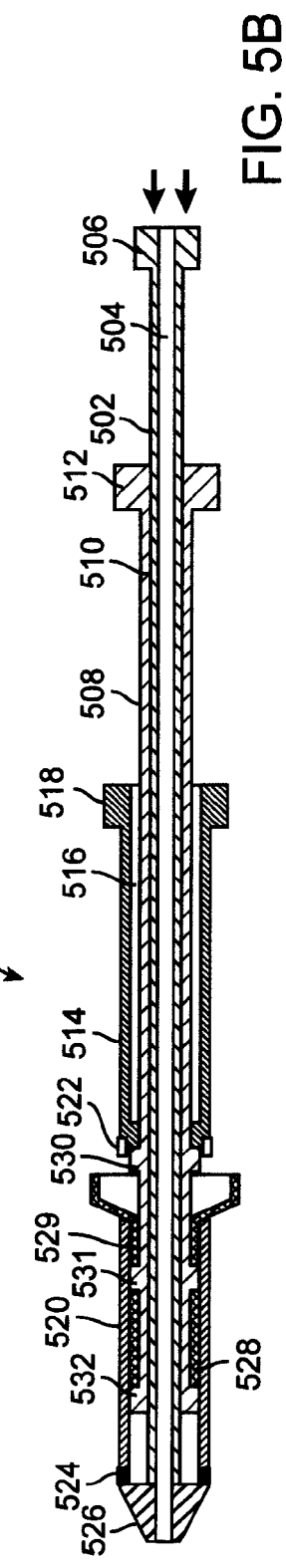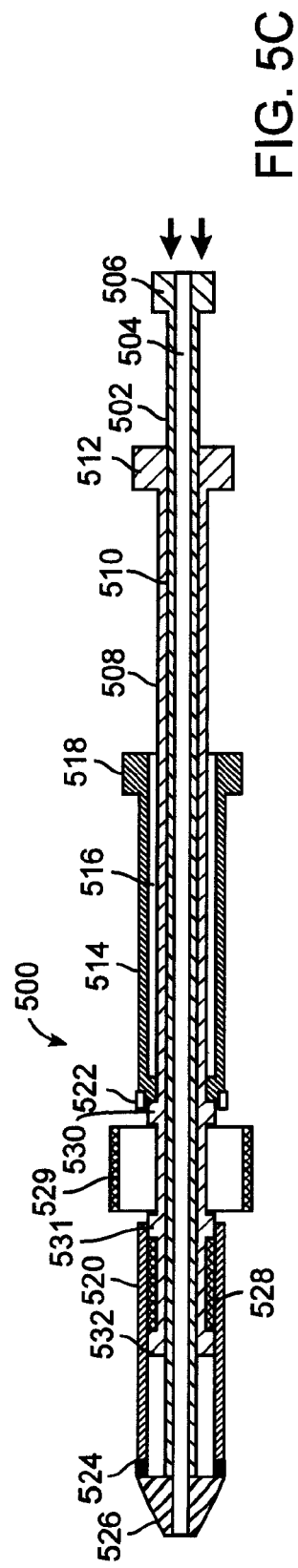

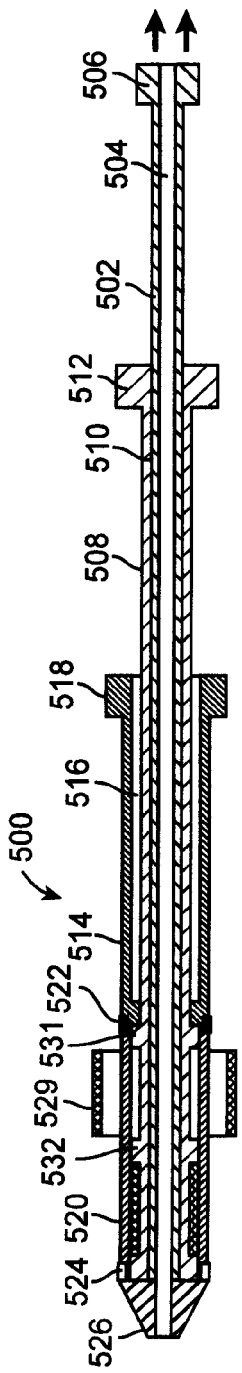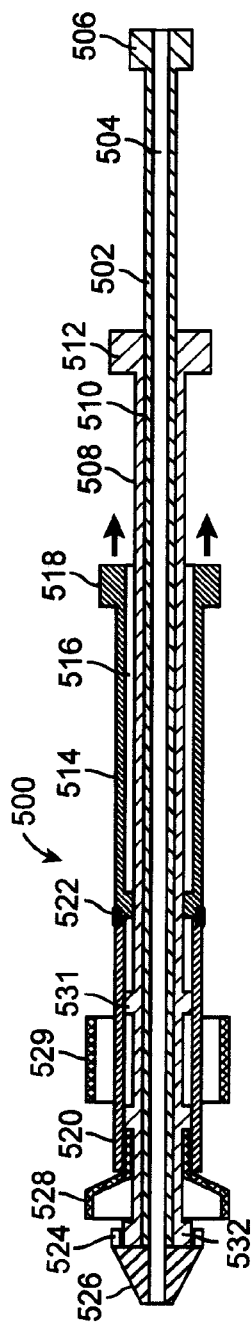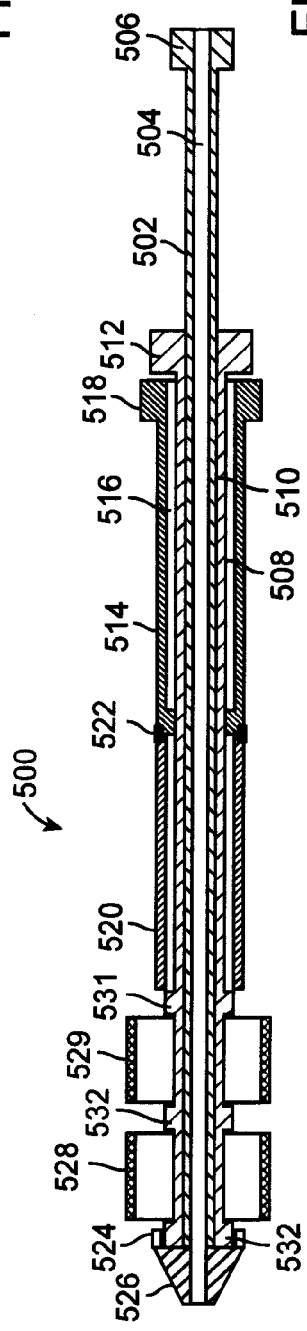

FIG. 10B
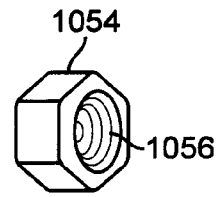
FIG. 10C
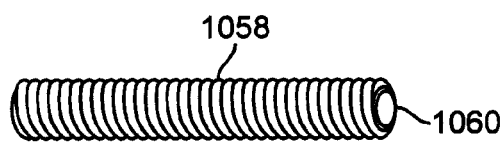
FIG. 10D
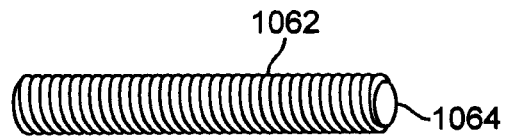
FIG. 10E
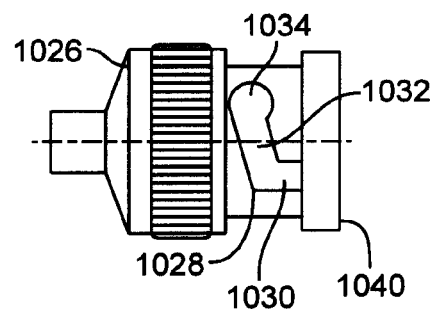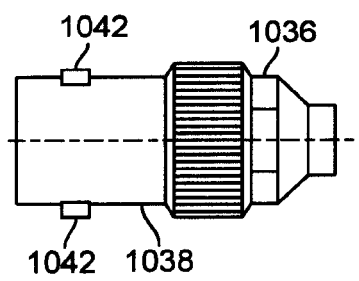
FIG. 10F

BI-DIRECTIONAL STENT DELIVERY SYSTEM

CROSS-REFERENCES TO RELATED APPLICATIONS

This is a Division of application Ser. No. 12/911,604, filed Oct. 25, 2010, now U.S. Pat. No. 8,864,811, which claims the benefit of priority of U.S. Provisional Patent Application No. 61/352,408, filed Jun. 8, 2010. The disclosures of the prior applications are hereby incorporated by reference herein in their entirety.

BACKGROUND OF THE INVENTION

1. Field of the Invention

The present invention relates generally to medical devices, and more particularly to endoluminal delivery systems for prostheses such as stents, or other implantable structures. The delivery systems may be used for placement of a stent in the arterial system, the venous system, or any other portion of the body. The use of stents and other implantable medical devices such as grafts, stent-grafts, filters, shunts, valves, etc., are referred to herein as prostheses. Prostheses may be used to deliver drugs to tissue, support tissue, or maintain patency of bodily lumens, as well as performing other functions, and have been widely reported in the scientific and patent literature.

Stents are typically delivered via a catheter in an unexpanded configuration to a desired location in the body. The combined stent and catheter is typically referred to as the stent delivery system. Once at the desired location, the stent is expanded and implanted into the body lumen. Examples of locations in the body include, but are not limited to, arteries (e.g. aorta, coronary, carotid, cranial, iliac, femoral, etc.), veins (e.g. vena cava, jugular, iliac, femoral, hepatic, subclavian, brachiocephalic, azygous, cranial, etc.), as well as other locations including the esophagus, biliary duct, trachea, bronchials, duodenum, colon, and ureter.

Typically, a stent will have an unexpanded configuration with reduced diameter for placement and an expanded configuration with expanded diameter after placement in the vessel, duct, or tract. Some stents are self-expanding, and some stents are mechanically expanded with a radial outward force applied from within the stent (e.g. with a balloon). Some stents have one or more characteristics common to both self-expanding and mechanically expandable stents.

Self-expanding stents are made from a material that is resiliently biased to return to a pre-set shape. These materials may include superelastic and shape memory materials that can expand to an implanted configuration upon delivery or through a change in temperature. Self-expanding stents are constructed from a wide variety of materials including nitinol (a nickel titanium alloy), spring steel, shape-memory polymers, etc.

In many stent delivery systems, particularly those used to deliver a self-expanding stent, the stent is typically retained on the catheter in its unexpanded form with a constraining member or other retention device such as a sheath or outer shaft. The stent may be deployed by retracting the outer shaft from over the stent. To prevent the stent from being drawn longitudinally with the retracting shaft, many delivery systems provide the catheter shaft with a pusher, bumper, hub, holder or other stopping element.

Precise delivery of stents can be challenging. In the case of balloon expandable stents, the stent may foreshorten as the stent radially expands, therefore, the change in length must be taken into account when deploying the stent at the treatment site. In the case of self-expanding stents, due to the elastic nature of the stents, they may "jump" away from the delivery catheter during deployment. For this reason, it would be desirable to provide improved stent delivery systems that can accurately deliver a prosthesis such as a stent to a desired treatment site. Additionally, depending on the anatomy being treated, this may add further challenges to accurate stent delivery. In certain parts of the anatomy, exact placement of the stent is critical to the successful clinical outcome of the procedure. For example, percutaneous coronary intervention (PCI) in ostial coronary artery lesions has been technically difficult because the stent is preferably precisely deployed in the ostium without side branch compromise. A similar level of accuracy is needed with ilio-femoral and ilio-caval stenting as is routinely used for the treatment of iliac vein compression syndrome (IVCS) and post-thrombotic syndrome (PTS) whereby the profunda and the inferior vena cava can be partially or completely blocked (or "stent jailed") by the stent if the stent is not placed accurately after deployment. Other examples where precise placement of the stent are important include but are not limited to any number of arterial applications, esophageal stenting of gastric varices, transjugular intrahepatic portosystemic shunt (TIPS) stenting for relief of portal hypertension, and use of endovascular stent-grafts for arterial aneurysms (e.g. AAA, femoral, popliteal).

Additionally, depending on the direction from which the delivery catheter approaches the treatment site, it may be desirable to deploy the stent in a preferred direction. Physicians may enter the body through different access sites, e.g. femoral vein or artery, the internal jugular vein (IJV), etc. before inserting the stent delivery system through the bodily lumens to the target location. Because the stent delivery system will be in different orientations depending on the physician's choice for access site, it may be necessary for the delivery system to have the correct stent release mode, such as proximal or distal release of the stent. It would therefore be advantageous for a delivery system to allow both release modes such that the operator (e.g. physician), can use the same system with either approach. With the typical commercially available stent delivery system, the operator is limited to one approach due to the distal release of the stent. Physician technique in stenting can also dictate which release is used in a procedure. For example, in the case of iliofemoral stenting with a femoral approach the user may choose to deploy and overlap multiple stents of varying sizes using proximal release such that the smaller diameter stent is placed first and the amount of overlap with the secondary stent(s) is tightly controlled.

In situations where multiple stents are delivered, it may be desirable to selectively deploy the stents. For example, abdominal aortic aneurysm (AAA) stent-grafts can be constructed of multiple components—trunk or main body, bifurcated main, main extension, limb extensions, stepped limbs, flared limbs, etc. Because each component is placed and deployed with a preferred release, one bi-directional deployment system with multiple stents, or stent grafts, or components could serve the function of numerous standard delivery systems. The deployment of the stents or components can be any combination of proximal or distal releases. This type of stenting can be useful in other areas of the body where bifurcations are present as well.

Furthermore, operators may require bi-directional deployment in cases where the target location is bookended by anatomical features that require exact stent placement of both the distal and proximal ends of the stent. Two bi-directional deployment systems may be used with one employing the distal release and the other employing the proximal release. The non-critical ends of each of the deployed stents would overlap with each other in the middle of the target location. Without bi-directional deployment capability, an operator would face the likelihood of understenting, overstenting, or inaccurate stent placement and suboptimal results because of the inexact lengths of stent available to treat an exact length of disease. As mentioned earlier, ilio-femoral and ilio-caval stenting of the venous system may require the user to stent entirely from the confluence of the inferior vena cava to the profunda of the leg. A distal release is preferred for accurate stent deployment at the confluence, whereas a proximal release is preferred so as to avoid "stent jailing" of the profunda. In lieu of performing this procedure with two bi-directional deployment systems, another bi-directional deployment device embodiment loaded with two stents (one deployable with distal release and one deployable with proximal release) could greatly simplify this type of procedure.

Therefore, it would be desirable to deploy a stent from its distal end toward its proximal end, as is traditionally done in many conventional stent procedures. In other cases, it would be desirable if the stent could be deployed from its proximal end toward its distal end. In the case where multiple stents are deployed, it would be desirable if a first stent could be deployed in a first direction, and a second stent deployed in a second direction that may be the same or different than the first direction. Thus, improved stent delivery systems such as a bi-directional stent deployment system, also referred to as bi-modal, or selectively deployable stent delivery system would be advantageous. Additionally, since there currently are no FDA approved and commercially available stents and delivery systems for treating venous outflow obstruction, there is need for such devices and methods of use. At least some of these objectives will be met by the inventions described herein.

2. Description of the Background Art

Relevant patent applications include U.S. patent application Ser. No. 12/903,056, filed Oct. 12, 2010, the entire contents of which are incorporated herein by reference. Other relevant patents and publications include U.S. Pat. Nos. 7,137,993; 6,849,084; 6,716,238; 6,562064; 5,873,907; and U.S. Patent Publication Nos. 2009/0264978; 2004/220585; 2002/120323; and 2002/188341.

BRIEF SUMMARY OF THE INVENTION

The present invention relates generally to medical devices, and more particularly to endoluminal delivery systems for prostheses such as stents, or other implantable structures. The delivery systems may be used for placement of a stent in the arterial system, the venous system, or any other portion of the body.

In a first aspect of the present invention, a bi-directional stent delivery system comprises an inner elongate shaft having a proximal portion and a distal portion, and a radially expandable prosthesis disposed over the inner elongate shaft. The prosthesis has a radially collapsed configuration and a radially expanded configuration. In the collapsed configuration the prosthesis is adapted to be delivered through a patient's vasculature, and in the expanded configuration the prosthesis engages a vessel wall or other tissue. An outer elongate shaft has a proximal portion and a distal portion. A shuttle sheath has a proximal portion and a distal portion. The shuttle sheath is disposed over the radially expandable prosthesis. The distal portion of the inner shaft is releasably coupled to the distal portion of the shuttle sheath, and the distal portion of the outer shaft is releasably coupled the proximal portion of the shuttle sheath. Distal advancement of the inner shaft advances the shuttle sheath distally when the outer shaft is uncoupled from the shuttle sheath, thereby allowing the prosthesis to radially expand from a proximal end thereof to a distal end thereof. Proximal retraction of the outer shaft retracts the shuttle sheath proximally when the inner shaft is uncoupled from the shuttle sheath, thereby allowing the prosthesis to radially expand from a distal end thereof to a proximal end thereof.

The inner shaft may comprise a lumen extending between the proximal and distal portions that is configured to slidably receive a guidewire. The prosthesis may comprise a first stent. A second stent may also be included with the system, and the second stent may be unattached and axially separated from the first stent by a gap. The stents may be self-expanding, balloon expandable, or a combination thereof. The stents may be fabricated from a nickel titanium alloy such as nitinol.

The outer shaft may comprise a lumen extending between the proximal and distal portions thereof. The shuttle sheath may have a length that is equal to or greater than the length of the radially expandable stent or stents. The shuttle sheath may constrain the prosthesis along substantially its entire length. The shuttle sheath may have a proximal end, a distal end, and a lumen extending therebetween. The shuttle sheath may comprise a substantially cylindrical sheath.

The system may further comprise a distal coupling mechanism that releasably couples the distal portion of the inner shaft to the distal portion of the shuttle sheath. The distal coupling mechanism may comprise a threaded or helical region on the distal portion of the inner shaft and a corresponding threaded or helical region on the distal portion of the shuttle sheath. The distal coupling mechanism may comprise one or more of a snap fit, an interference fit, a barbed connector, a locking mechanism, a rotatable key lock, a linear key lock, a threaded bushing, a twist lock, a magnetic coupling, a bayonet coupling, or a frangible connector. The system may further comprise a proximal coupling mechanism that releasably couples the distal portion of the outer shaft to the proximal portion of the shuttle sheath. The proximal coupling mechanism may comprise a threaded or helical region on the distal portion of the outer shaft and a corresponding threaded or helical region on the proximal portion of the shuttle sheath. The proximal coupling mechanism may comprise one or more of a snap fit, an interference fit, a barbed connector, a locking mechanism, a rotatable key lock, a linear key lock, a threaded bushing, a twist lock, a magnetic coupling, a bayonet coupling, or a frangible connector.

The inner shaft may be threadably or helically engaged with the shuttle sheath, and the outer shaft may also be threadably or helically engaged with the shuttle sheath. The threads or helix engaging the inner shaft with the shuttle sheath may have a first orientation, and the threads or helix engaging the outer shaft with the shuttle sheath may have a second orientation opposite of the first orientation such that rotation of the inner shaft in a first direction couples the inner shaft with the shuttle sheath and rotation of the inner shaft in a second direction opposite the first direction disengages the inner shaft from the shuttle sheath. Additionally rotation of the outer shaft in the first direction may disengage the outer shaft from the shuttle sheath and rotation of the outer shaft in the second direction may engage the outer shaft with the shuttle sheath. The inner shaft may be coupled to the shuttle sheath with a bayonet coupling mechanism that has a slot in a first orientation, and the outer shaft may be coupled with the shuttle sheath with a second bayonet coupling mechanism having a slot in a second orientation opposite the first slot. Rotation of the inner shaft in a first direction may couple the inner shaft with the shuttle sheath and rotation of the inner shaft in a second direction opposite the first direction may disengage the inner shaft from the shuttle sheath. Rotation of the outer shaft in the first direction may disengage the outer shaft from the shuttle sheath and rotation of the outer shaft in the second direction may engage the outer shaft with the shuttle sheath.

The system may further comprise a middle shaft concentric with the inner and the outer shafts, and disposed therebetween. The prosthesis may be disposed over the middle shaft and in direct engagement therewith. The middle shaft may comprise an outer surface that is substantially smooth. The middle shaft may comprise a proximal stent stop and a distal stent stop. The proximal stop may be disposed proximally of a proximal end of the prosthesis, and the distal stopping element may be disposed distally of a distal end of the prosthesis. The proximal stopping element may prevent proximal movement of the prosthesis, and the distal stopping element may prevent distal movement of the prosthesis. The proximal stopping element or the distal stopping element may comprise one or more of a ring, a band, a step, a bushing, or a sleeve, that prevent proximal or distal movement of the prosthesis.

The system may also comprise an actuator mechanism disposed near a proximal end of the delivery system. The actuator mechanism may be operably coupled with the inner and outer shafts, thereby allowing an operator to couple and uncouple the inner and outer shafts with the shuttle sheath. The actuator mechanism may also be configured to slidably or rotatably move the inner and the outer shafts both proximally and distally. The system may further comprise an intravascular ultrasound device configured to allow visualization of the prosthesis and surrounding tissue.

In another aspect of the present invention, a bi-directional method for deploying a prosthesis at a treatment site in a patient comprises providing a delivery catheter comprising a prosthesis having a proximal end and a distal end, the prosthesis in a collapsed configuration and disposed on the delivery catheter. The prosthesis is delivered to the target treatment site, and a deployment direction for the prosthesis is selected. The deployment direction comprises radially expanding the prosthesis from the proximal end thereof to the distal end thereof, and radially expanding the prosthesis from the distal end thereof to the proximal end thereof. A constraint is removed from the prosthesis thereby permitting the prosthesis to radially expand in the selected deployment direction. The prosthesis radially expands from the collapsed configuration to an expanded configuration in the selected deployment direction so that the expanded prosthesis engages tissue at the target treatment site. The delivery catheter is withdrawn from the patient and the prosthesis is left deployed in the patient at the target treatment site.

Delivering the prosthesis may comprise advancing the delivery catheter through vasculature of the patient to the target treatment site. The delivery catheter may have a proximal end, a distal end, and a lumen therebetween. Delivering the prosthesis may comprise slidably advancing the delivery catheter over a guidewire disposed in the lumen. Delivering the prosthesis may comprise positioning the prosthesis in a vein, such as the iliac vein.

The delivery catheter may comprise an inner elongate shaft and a shuttle sheath disposed over the prosthesis. Selecting the deployment direction for the prosthesis may comprise coupling the inner elongate shaft with the shuttle sheath, distally advancing the inner elongate shaft distally thereby advancing the shuttle sheath distally away from the prosthesis, and radially expanding the prosthesis from the proximal end thereof to the distal end thereof. Coupling the inner elongate shaft with the shuttle sheath may comprise threadably or helically engaging the inner elongate shaft with the shuttle sheath or coupling them together with a bayonet coupling. The delivery catheter may further comprise an outer elongate shaft, and selecting the deployment direction may comprise decoupling the outer elongate shaft from the shuttle sheath. Decoupling the outer elongate shaft from the shuttle sheath may comprise threadably or helically disengaging the outer elongate shaft from the shuttle sheath. Decoupling may comprise releasing a bayonet coupling between the outer elongate shaft and the shuttle sheath.

The delivery catheter may comprise an outer elongate shaft and a shuttle sheath disposed over the prosthesis. Selecting the deployment direction for the prosthesis may comprise coupling the outer elongate shaft with the shuttle sheath, proximally retracting the outer elongate shaft thereby retracting the shuttle sheath proximally away from the prosthesis, and radially expanding the prosthesis from the distal end thereof to the proximal end thereof. Coupling the outer elongate shaft with the shuttle sheath may comprise threadably or helically engaging the outer elongate shaft with the shuttle sheath. Coupling may comprise coupling the inner elongate shaft and the shuttle sheath with a bayonet coupling. The delivery catheter may further comprise an inner elongate shaft, and selecting the deployment direction may comprise decoupling the inner elongate shaft from the shuttle sheath. Decoupling the inner elongate shaft from the shuttle sheath may comprise threadably or helically decoupling the inner elongate shaft from the shuttle sheath. Decoupling may comprise releasing a bayonet coupling between the outer elongate shaft and the shuttle sheath.

The delivery catheter may comprise a shuttle sheath that is disposed over the prosthesis, and removing the constraint may comprise distally advancing the shuttle sheath away from the prosthesis so that the prosthesis is unconstrained from radial expansion in a direction extending from the proximal end of the prosthesis to the distal end of the prosthesis. The delivery catheter may comprise a shuttle sheath disposed over the prosthesis, and removing the constraint may comprise proximally retracting the shuttle sheath away from the prosthesis so that the prosthesis is unconstrained from radial expansion in a direction extending from the distal end of the prosthesis to the proximal end of the prosthesis.

Radially expanding the prosthesis may comprise self-expanding a stent. Withdrawing the delivery catheter from the patient may comprise withdrawing the delivery catheter from the patient's vasculature. The prosthesis may comprises two prostheses, and the method may comprise selecting a first deployment direction for the first prosthesis, radially expanding the first prosthesis in the first deployment direction, and radially expanding the second prosthesis in a second deployment direction opposite of the first deployment direction. The method may comprise visualizing the expanded prosthesis with various techniques including ultrasound or fluoroscopy. The method may also comprise retracting the radially expanded prosthesis into a shuttle sheath, repositioning the prosthesis, and radially expanding the prosthesis. The radially expanded prosthesis may be dilated with an expandable member such as a balloon.

These and other embodiments are described in further detail in the following description related to the appended drawing figures.

BRIEF DESCRIPTION OF THE DRAWINGS

FIGS. 2A-2D illustrate the embodiment of FIGS. 1A-1D configured for proximal stent release.

FIGS. 3A-3E illustrate an exemplary embodiment of a bi-directional stent delivery catheter configured for distal stent release.

FIGS. 4A-4E illustrate the embodiment of FIGS. 3A-3E configured for proximal stent release.

FIGS. 5A-5F illustrate an exemplary embodiment of a bi-directional stent delivery catheter for delivery of multiple stents.

FIG. 10A-10E illustrates exemplary embodiments of threaded coupling mechanisms.

FIG. 10F illustrates an exemplary embodiment of a bayonet coupling mechanism.

DETAILED DESCRIPTION OF THE INVENTION

The present invention relates generally to medical devices, and more particularly to endoluminal delivery systems for prostheses such as stents, or other implantable structures. The delivery systems may be used for placement of a stent in the arterial system, the venous system, or any other portion of the body. The use of stents and other implantable medical devices such as grafts, stent-grafts, filters, shunts, valves, etc., are referred to herein as prostheses. Prostheses may be used to deliver drugs to tissue, support tissue, or maintain patency of bodily lumens, as well as performing other functions, and have been widely reported in the scientific and patent literature.

FIGS. 1A-1D and FIGS. 2A-2D illustrate a first exemplary embodiment of a bi-directional delivery system for a prosthesis. Delivery of a stent will be described, however, one of skill in the art will appreciate that the system may be used to deliver other prosthesis such as grafts, stent grafts, filters, etc. FIGS. 1A-1D illustrate distal release of a stent where the stent is deployed such that the stent expands from its distal end toward its proximal end. FIGS. 2A-2D illustrate proximal release of a stent where the stent is deployed such that the stent expands from is proximal end toward its distal end.

Figure 1A:
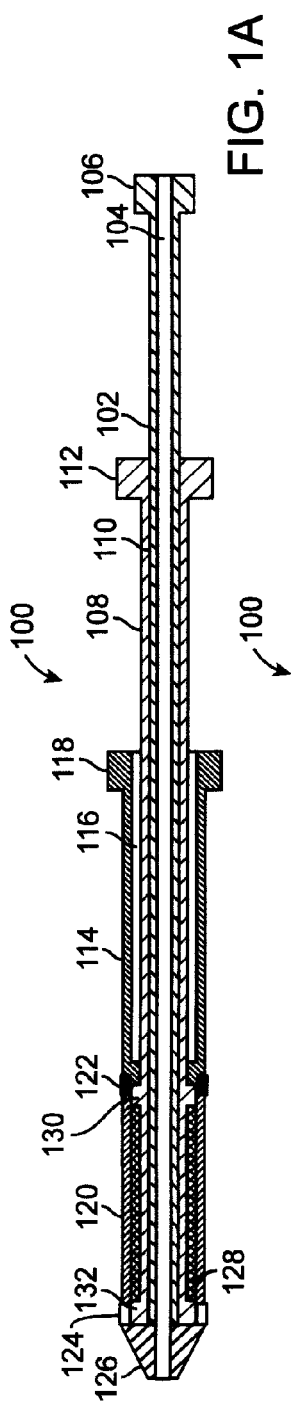
FIGS. 1A-1D illustrate an exemplary embodiment of a bi-directional stent delivery catheter configured for distal stent release.

FIG. 1A illustrates a stent delivery system 100 which is configured to preferentially deploy a stent distally. The delivery system 100 includes an inner shaft 102, a middle shaft 108, and outer shaft 114, a shuttle sheath 120 and a stent 128. The shafts may be extruded tubes preferably having circular cross sections, or other cross sections are contemplated such as oval, rectangular, elliptical, etc. The shafts in this and other embodiments described below may be fabricated from polyethylene, PTFE, FEP, PVC, or other materials known in the art. The inner shaft 102 has a central lumen extending from its proximal end to its distal end for fluids such as contrast media or for slidably receiving a guidewire (not illustrated). A distal tapered nosecone 126 is coupled with inner shaft 102 and prevents trauma to the vessel or other tissue during delivery. A hub 106 or flared region provides the user a region for grasping, and also provides a stop for preventing the inner shaft from being advanced too far distally into the middle shaft 108 (or retracting the middle shaft too far proximally). The middle shaft 108 also has a central lumen 110 extending between its proximal and distal ends, and the middle shaft 108 is slidably disposed over the inner shaft 102. The middle shaft 108 also has a hub 112 or flared region that provides the user a region for grasping, as well as providing a stop to prevent the middle shaft 108 from being advanced too far distally into the outer shaft 114 (or retracting the outer shaft 114 too far proximally). The middle shaft 108 is slidably disposed over the inner shaft 102, and slidably disposed in the outer shaft 114 and also slidably disposed in the shuttle sheath 120. This embodiment and others described below are configured for over the wire use, although one of skill in the art will appreciate that the delivery catheters may easily be modified to allow rapid exchange use with a guidewire. Rapid exchange and over the wire use are well described in the patent literature, such as in U.S. Pat. No. 5,451,233. Additionally, the various hubs 106, 112, 118 may include hemostasis valves which allow the shafts to move relative to one another while preventing blood or other fluids from exiting the proximal portion of the delivery catheter. A hemostasis valve such as a Tuohy-Borst may also be used to tighten down on a shaft to prevent the shaft from moving relative to another shaft. Therefore, the Tuohy-Borst may be used as a locking mechanism as well.

A stent 128 is disposed over the middle shaft 108 in a collapsed configuration sized for delivery. A pair of stops 130, 132 prevent the stent 128 from moving proximally or distally along the middle shaft 108 during delivery and deployment. The stops 130, 132 may be rings, bands, steps, bushings, sleeves, bumps, flanges, raised annular sections, or other structures which prevent the stent 128 from sliding along the middle shaft 108. The stops 130, 132 may be radiopaque to allow visualization of the proximal and distal ends of the stent under fluoroscopy during the stent procedure. Other visualization techniques may also be used such as x-ray, endoscopy, IVUS, MRI, ultrasound, and CT, as well as other techniques. Stent 128 is preferably a self expanding stent and therefore shuttle sheath 120 is disposed over the stent 128 in order to constrain it and prevent radial expansion thereof. The stent 128 may be fabricated from self expanding or shape memory alloys such as nitinol, spring steels, resilient polymer, or other materials known in the art. The shuttle sheath 120 is at least as long or longer than the length of the stent 128.

Outer shaft 114 also has a central lumen 116 extending between the proximal and distal ends of the shaft 114 so that the middle shaft 108 may be slidably disposed therein. A hub 118 on the proximal end of the outer shaft 114 provides the user a region for grasping, and also prevents the hub 112 on the middle shaft 108 from being advanced too far distally (or prevents the outer shaft 114 from being retracted proximally too far).

A proximal lock or coupling mechanism 122 couples the distal end of the outer shaft 113 with the proximal end of the shuttle sheath 120. A distal lock or coupling mechanism 124 couples distal end of the shuttle sheath 120 with the distal end of the inner shaft 102 via nosecone 126. The proximal and distal locks or coupling mechanisms may take a number of forms, including for example, snap fits, interference fits, barbed connectors, locking mechanisms, key locks, rotational or linear locks, threaded bushings, twist locks, magnetic couplings, bayonet coupling, breakable or frangible connectors, as well as others known in the art. The proximal coupling may take the same form as the distal coupling, or different couplings may be used on the proximal and distal ends. In this embodiment, the proximal lock 122 is locked (as indicated by the darkened rectangle 122), and the distal lock 124 is unlocked (as indicated by the white rectangle 124). This configuration allows preferential distal delivery of stent 128 as illustrated in FIGS. 1B-1D.

Figure 1B:
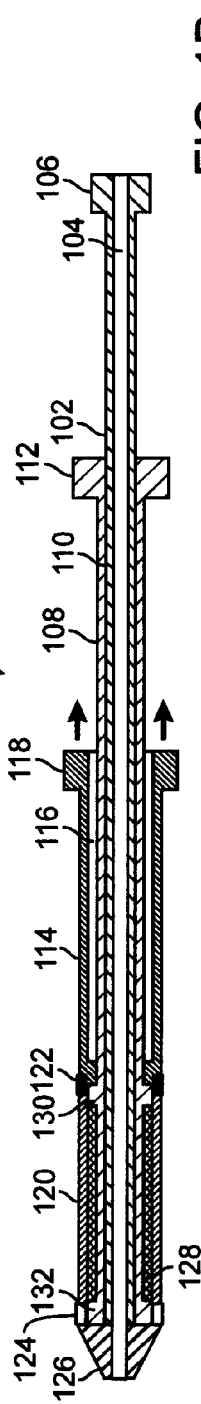
Figure 1C:
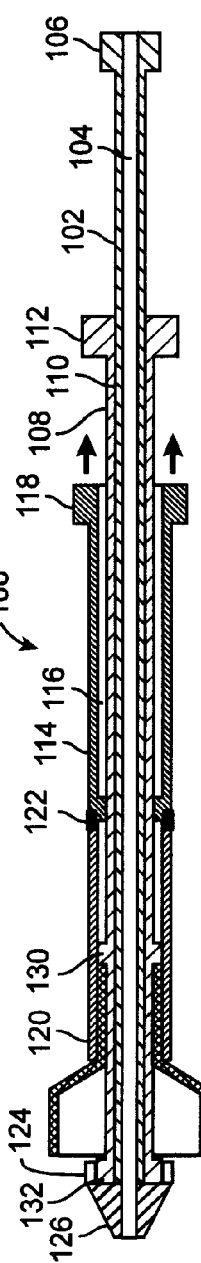
Figure 1D:
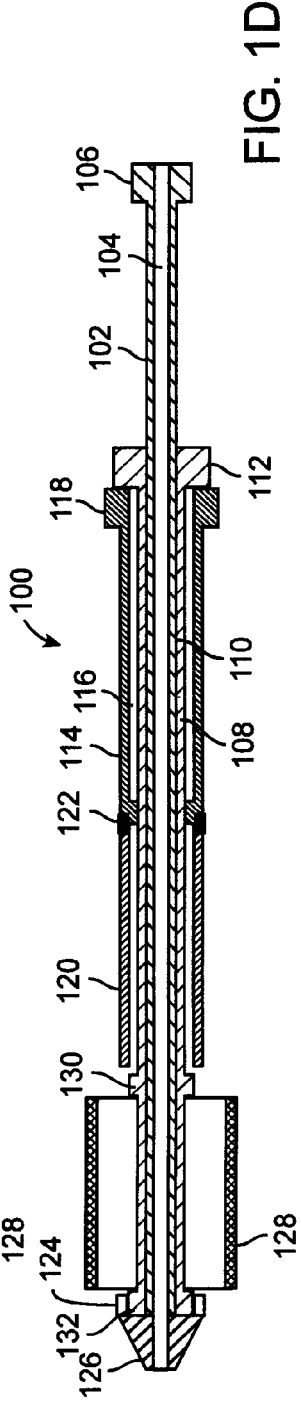

In FIG. 1B, the outer shaft 114 is retracted proximally relative to the middle shaft 108 and the inner shaft 102. Because outer shaft 114 is locked with shuttle sheath 120, and shuttle sheath 120 is unlocked from inner shaft 102, as the outer shaft 114 is proximally retracted, shuttle sheath 120 will also be proximally retracted. FIG. 1C shows that as shuttle sheath 120 is proximally retracted, stent 128 become partially unconstrained, allowing stent 128 to self expand into its radially expanded configuration. In this partially expanded configuration, a physician may optional re-advance the shuttle sheath 120 distally in order to draw the stent 128 back into a collapsed configuration constrained by shuttle sheath 120. This allows the stent to be repositioned if the initial deployment is not optimal. As shuttle sheath 120 continues to move proximally, stent 128 will also continue to self expand from its distal end toward its proximal end. FIG. 1D shows that once shuttle sheath 120 is fully retracted proximally and stent 128 is completely unconstrained, stent 128 fully expands into its radially expanded configuration. The delivery catheter 100 may then be retracted proximally through expanded stent 128 and removed from the patient. A handle (not illustrated) may be provided on the proximal end of the catheter with various actuation mechanisms (e.g. rotating knobs, sliding levers, etc.) to facilitate actuation of the shafts relative to one another. The handle may also be used with other embodiments disclosed herein. This delivery method may be used with a typical antegrade femoral vein approach. Distal release may also be used for stenting above the origin of the profunda when using a retrograde approach.

FIGS. 2A-2D illustrate the delivery system 100 configured preferentially for proximal delivery of a stent. FIG. 2A shows the delivery system 100 that is substantially the same as previously described above with respect to FIGS. 1A-1D, except the major difference being that the configuration of the proximal and distal locks or couplings 122, 124 has been reversed. In this exemplary embodiment, the distal lock 124 is now in a locked configuration such that shuttle sheath 120 is coupled with inner shaft 102 via nosecone 126. The locked configuration is indicated by the blackened rectangle 124. Proximal lock 122 is unlocked, therefore the shuttle sheath 120 is uncoupled from the outer shaft 114, as indicated by the white rectangle 122.

In FIG. 2B, the inner shaft 102 is advanced distally thereby also distally advancing shuttle sheath 120 relative to stent 128, as seen in FIG. 2C. As shuttle sheath 120 advanced distally, stent 128 becomes unconstrained, thereby allowing the unconstrained portion of stent 128 to self expand from its proximal end toward its distal end, into its radially expanded configuration. Additionally, when stent 128 is in a partially expanded configuration as shown in FIG. 2C, a physician optionally may proximally retract inner shaft 102 thereby retracting shuttle sheath 120 over stent 128 to recapture the stent and re-constrain the stent 128 in its collapsed configuration. This allows the physician to reposition the stent when its initial deployment is not optimal. FIG. 2D illustrates the stent 128 in its fully expanded configuration after shuttle sheath has been advanced distally so that stent 128 is unconstrained. The catheter 100 may then be retraced proximally through expanded stent 128 and removed from the patient. This method of delivery may be used during a contralateral retrograde venous approach or a jugular approach. Placement of the stent above the origin of the profunda vein is critical, therefore proximal release may also be used when using an antegrade approach.

In the examples illustrated in FIGS. 1A-1D and FIGS. 2A-2D, the proximal and distal locks or coupling mechanisms 122, 124 are pre-set to a locked or unlocked configuration. One of skill in the art will appreciate that any combination of locked and unlocked configurations is possible. Therefore the catheter may be supplied with both locks in the locked position, or both in the unlocked position. Also, the catheter may be supplied with proximal lock locked and the distal lock unlocked, or the catheter may be supplied with the proximal lock unlocked and the distal lock locked. The user may use the catheter as supplied, or the lock configuration may be changed by the user either prior to using the catheter, or in situ, depending on the desired stent deployment direction. Examples of various locking mechanisms application to this embodiment as well as the other embodiments disclosed herein are described in greater detail below.

FIGS. 3A-3E illustrate another exemplary embodiment of a bi-directional stent delivery system. The delivery system 300 may be used for either proximal or distal stent delivery depending on how the shafts are actuated. FIG. 3A illustrates the delivery system 300 prior to use in its preferred configuration. The system 300 includes an inner shaft 302, a middle shaft 308, an outer shaft 314, a shuttle sheath 320, and a stent 328. Each of the shafts 302, 308, 314 have a lumen extending between the proximal and distal ends of the shaft to allow the shafts to slidably receive one another and slidably move relative to one another. For example, inner shaft 302 is slidably disposed in the lumen of middle shaft 308, and middle shaft is slidably disposed in the lumen of outer shaft 314. Additionally, each shaft 302, 308, 314 also has a hub or flanged region 306, 312, 318 near the proximal end of the shaft and provides a region for an operator to grasp, as well as providing a stop to prevent the shafts from moving too far into one another. Other aspects of the hubs are generally similar to those previously described.

Stent 328 is constrained and held in a radially contracted configuration on the middle shaft 308 by shuttle sheath 320. Stent stops 330, 332 generally take the same form as those previously described above in FIGS. 1A-1D and 2A-2D. The stops 330, 332 prevent unwanted axial movement of stent 328 relative to middle shaft 308. A lock or coupling mechanism 324 couples the distal end of shuttle sheath 320 with the inner shaft 302 via nose cone 326. In this preferred embodiment, the lock is closed (as indicated by the darkened rectangle) so that shuttle sheath 320 is connected to inner shaft 302 via nose cone 326. The stent 328 generally takes the same form as stent 128 previously described above.

In FIG. 3B the inner shaft 302 is advanced distally. Because lock 324 is closed, shuttle sheath 320 will also move distally. As the shuttle sheath 320 is advanced distally, stent 328 will become unconstrained and will start to self-expand slightly until further expansion is constrained by outer shaft 314. As inner shaft 302 is further advanced distally, stent 328 becomes completely unconstrained and self expands into engagement with outer shaft 314 where further self expansion is prevented, as shown in FIG. 3C.

Outer shaft 314 may then be proximally retracted as illustrated in FIG. 3D. Proximal retraction of outer shaft 314 releases the constraint on stent 328 so that the stent may then self expand into its radially expanded configuration proximally. In FIG. 3D, the stent 328 is partially expanded and partially constrained. In this configuration, the operator may optionally re-advance the outer shaft 314 to recapture and reconstrain stent 328 into a collapsed configuration. This allows the stent 328 to be repositioned and redeployed if the initial position was not optimal. The outer shaft 314 is then fully retracted proximally so that stent 328 is fully unconstrained, and stent 328 radially expands into its fully expanded configuration. Catheter 300 may then be proximally retracted through the stent 328 and removed from the patient.

The lock 324 in FIGS. 3A-3E is preferably in the locked configuration so that proximal or distal movement of the inner shaft 302 will correspondingly move the shuttle sheath 320. One of skill in the art will appreciate that the catheter may be provided with the lock in the unlocked configuration, and the user may lock it as desired.

FIGS. 4A-4E illustrate how delivery catheter 300 in FIGS. 3A-3E may also be used for proximal stent deployment. The delivery system 300 in FIGS. 4A-4E is the same as the system described above in FIGS. 3A-3E, except that the order of shaft actuation is different, thereby allowing stent deployment in the opposite direction.

FIG. 4A shows the stent delivery system 300 prior to use. In FIG. 4B, the outer shaft 314 is proximally retracted until the shuttle sheath 320 is unconstrained by the outer shaft 314, as seen in FIG. 4C. In FIG. 4D, the inner shaft 302 is advanced distally. Because lock 324 is locked with shuttle sheath 320 via nose cone 326, the shuttle sheath 320 will also be advanced distally, thereby allowing stent 328 to self expand as the constraint provided by shuttle sheath 320 is removed. Also, as previously mentioned, while the stent is partially expanded, a physician may optionally recapture the stent and reposition it when the initial deployment is not optimal. The stent 328 may be recaptured by retracting the inner shaft 302, thereby also proximally retracting shuttle sheath 320 so that stent 328 returns to its collapsed configuration constrained by shuttle sheath 320. In FIG. 4E, the inner shaft is advanced distally so that shuttle sheath 320 is removed from stent 328. Stent 328 is then unconstrained and can radially expand fully into its expanded configuration. Delivery catheter 300 may then be retracted proximally through stent 328 and removed from the patient.

FIGS. 5A-5F illustrate another exemplary embodiment of a bi-directional stent delivery system 500. This embodiment is similar to that previously described above in FIGS. 1A-1D and FIGS. 2A-2D, with the major difference being that this embodiment delivers two stents, one preferably with proximal release and the other preferably with distal release. FIG. 5A shows stent delivery system 500 having an inner shaft 502, a middle shaft 508, an outer shaft 514, a shuttle sheath 520, and two stents 528, 529. All three shafts 502, 508, 514 have a central lumen extending between the proximal and distal ends of the shafts in order to allow the shafts to move relative to one another. Inner shaft 502 is slidably disposed in the lumen of middle shaft 508, and middle shaft 508 is slidably disposed in the lumen of outer shaft 514. Also, a hub or flanged region 506, 512, 518 on the proximal end of each shaft 502, 508, 514 provides a region for the physician to grasp during usage and actuation, as well as providing a stop to prevent excessive shaft movement. Moreover, in this embodiment, as well as the previous embodiments, the hubs may have standard fittings on them such as Luer tapers or threaded portions for coupling with a syringe, tube, or other device. Other features of the hubs previously described may also be employed in this embodiment.

Stents 528, 529 are disposed over middle shaft 508, and stent stops 530, 531, 532 prevent unwanted axial movement of the stents along the middle shaft 514. The stents 528, 529 and stent stops 530, 531, 532 generally take the same form as those previously described above. Locks or coupling mechanisms 522, 524 couple the shuttle sheath 520 with either the inner shaft 502 or the outer shaft 514 as will be described in greater detail below. In FIG. 5A, lock 524 is closed or locked (as indicated by the darkened rectangle) such that shuttle sheath 520 is connected to inner shaft 502 via nose cone 526. Lock 522 is unlocked (as indicated by the white rectangle) such that outer shaft 514 is free to move relative to shuttle sheath 520.

In FIG. 5B, inner shaft 502 is advanced distally, thereby correspondingly advancing shuttle sheath 520 distally. As the proximal most stent 529 becomes unconstrained, it partially self expands into its radially expanded configuration. At this point, the physician may optionally retract the inner shaft 502 to recapture and constrain the stent 529 into its radially collapsed configuration if repositioning is desired. Otherwise, the inner shaft 502 is advanced distally until stent 529 becomes fully unconstrained and it radially expands into its expanded configuration as illustrated in FIG. 5C. Inner shaft 502 may further be advanced distally to permit distal release the distal most stent 528, or as seen in FIG. 5D, the inner shaft is proximally retracted and the distal lock or connector 524 is unlocked (illustrated by the white rectangle) and the proximal lock or connector 522 is locked (illustrated by the darkened rectangle).

In FIG. 5E the outer shaft 514 is then retracted proximally, thereby also proximally retracting shuttle heath 520 so that stent 528 becomes unconstrained. This permits stent 528 to radially self expand. While the stent 528 is partially expanded and partially collapsed, the outer shaft 514 may optionally be advanced distally to recapture and reconstrain the stent 528 in the radially collapsed configuration in case repositioning is desired. Otherwise, as seen in FIG. 5F, the outer shaft 514 is further retracted proximally until stent 528 is no longer constrained, and it self-expands into the radially expanded configuration, in a proximal direction (opposite of the first stent 529). Delivery system 500 may then be retracted proximally through stents 528, 529 and removed from the patient.

In this embodiment, one of skill in the art will appreciate that any order of stent deployment may be used. For example, both stents may be deployed proximally, or both may be deployed distally. In still other embodiments, the proximal stent may be deployed proximally while the distal stent is deployed distally. In yet other embodiments the proximal stent may be deployed distally, and the distal stent may be deployed proximally. Deployment direction will depend on the order of actuation of the shafts and the coupling and uncoupling of the shuttle sheath with the inner and outer shafts. Furthermore, any number of stents may be carried by the delivery system, and the exemplary embodiment is not intended to limit the system to delivery of two stents.

Figure 10A:
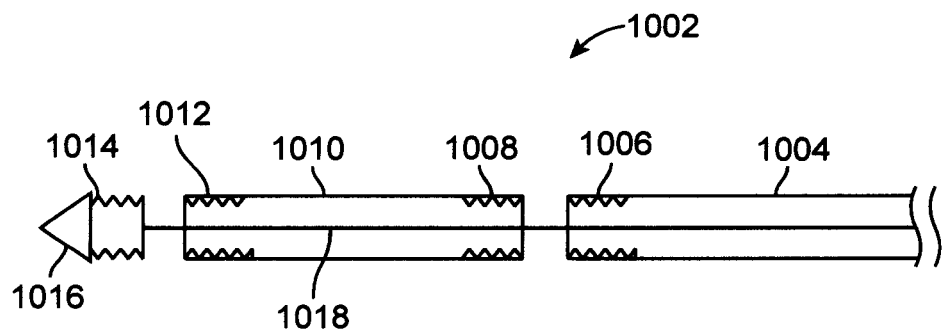

Any of the embodiments described above may have a number of different locking mechanisms or couplings that releasably join the shuttle sheath with the either the inner shaft or the outer shaft. For example, FIG. 10A illustrates how threaded couplings may be used. The delivery catheter 1002 includes an outer shaft 1004, inner shaft 1018, shuttle sheath 1010, and nose cone 1016 coupled to the inner shaft 1018. The middle shaft and stent described in embodiments above have been omitted for clarity. The outer shaft 1004 includes a threaded distal portion 1006 and the proximal portion of shuttle sheath 1010 also includes a threaded portion 1008. The distal portion of the shuttle sheath 1010 also includes a threaded portion 1012, and a proximal portion of nose cone 1016 includes a threaded portion 1014. The outer shaft 1004 may be rotated and advanced distally relative to the shuttle sheath 1010 thereby threadably engaging the outer shaft 1004 with the shuttle sheath 1010. Similarly, the inner shaft 1018 may be rotated and retracted proximally relative to the shuttle sheath, thereby threadably engaging the nose cone 1016 and inner shaft 1004 with the shuttle sheath 1010. The threads may be in same direction, or preferably are in different directions so that rotation in one direction couples the shuttle sheath with one of the shafts, and uncouples the shuttle sheath with the remaining shaft. Similarly rotation in the opposite direction uncouples the sheath from one shaft, and couples it with the remaining shaft. The threads often are either left handed or right handed. Additionally, in systems where the couplings are pre-set, the couplings may be uncoupled or coupled together. Male or female threads may be interchanged on the shuttle sheath and corresponding shaft.

FIGS. 10B-10E illustrate exemplary embodiments of threaded couplings which may be used on either end of the shuttle sheath, the inner shaft, or outer shaft to create the coupling mechanism in any of the embodiments described herein. For example, FIG. 10B illustrates a threaded tube 1050 with internal threads 1052, and FIG. 10C illustrates a threaded nut 1054 also with internal threads 1056. Threaded rods such as in FIGS. 10D-10E may be threadably engaged with the embodiments of FIGS. 10B-10C. FIG. 10D illustrates a threaded rod 1058 having external threads and a central channel 1060 extending through the threaded rod. FIG. 10E illustrates another threaded rod 1062 having external threads, but having a solid center 1064.

Another exemplary embodiment of a coupling or locking mechanism that may be used with any of the embodiments of delivery systems described above is illustrated in FIG. 10F. In this embodiment, a bayonet coupling, sometimes also referred to as a screw-snap connector, or BNC connector is used to releasably couple the shuttle sheath with either the inner shaft or the outer shaft, or both. The bayonet coupling includes a female connector 1026 and a male connector 1036. The female connector 1026 includes a central channel 1040 and at least one, and preferably two or more slotted channels 1028 that extend through a sidewall of the female connector 1026. The slotted channel 1028 has a linear portion 1030 which is generally parallel to the longitudinal axis of the connector 1026, a transverse portion 1032 which is disposed at an angle relative to the linear portion 1030, and a receiver 1034. The male connector 1036 includes an elongate distal portion 1038 that may be received in the central channel 1040 of the female connector 1026. At least one, and preferably two or more pins 1042 extend radially outward from the elongate distal portion 1038. In use, the male connector 1036 is inserted into the female connector 1026 such that the elongate distal portion 1038 is received in the central channel 1040. The pins 1042 are aligned with the linear portion 1030 of slot 1028, thus as the male connector is inserted into the female connector, the pin is advanced along the linear portion of the slot until it reaches the end of the linear portion. The male connector is then rotated relative to the female connector so that the pin then advances along the transverse portion of the slot until it reaches the end of transverse portion. A spring (not illustrated) is often included in the bayonet coupling, and this forces the male connector away from the female connector so that pin 1042 then nests in receiver 1034, locking the male and female connectors together. The two may be released from one another by pressing the male connector inward relative to the female connector and rotating the two relative to one another so that the pin slides outward along the transverse portion and then the two connectors are pulled apart relative to one another so that pin 1042 is released from the linear portion of the slot. Either the male or female connector may be used on one end of the shuttle sheath, with the opposite connector used on the inner or outer shaft to which the shuttle sheath is releasably connected. Additionally, just as threads have "handedness," the bayonet coupling may also have left-handed and right-handed mechanisms such that rotation in one direction releases the connector, while rotation in the opposite direction couples the connector. Thus a left handed bayonet coupling may be used on one end of the shuttle sheath, while a right handed bayonet coupling may be used on the opposite end of the shuttle sheath. This allows one end of the shuttle sheath to be connected without connecting the opposite end.

Figure 10G:
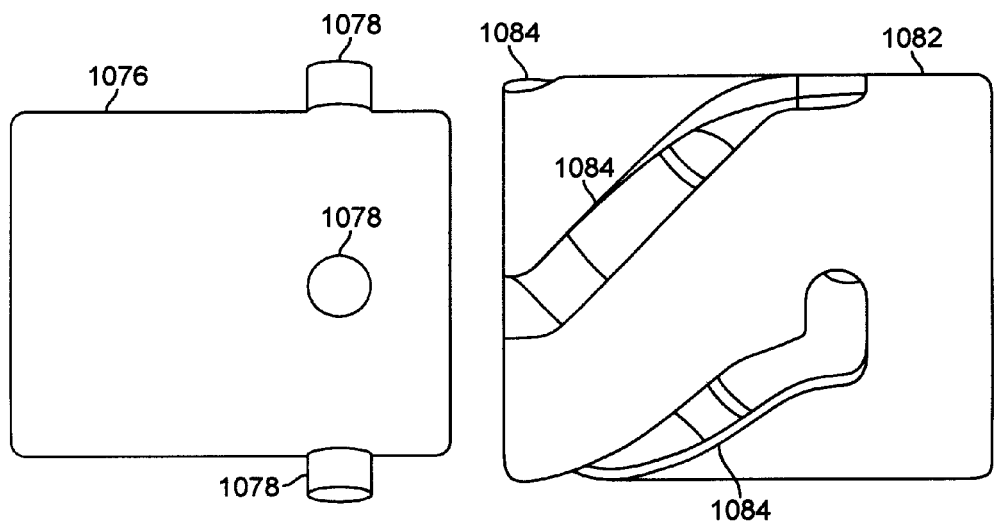
FIGS. 10G-10H illustrate another exemplary embodiment of a bayonet coupling mechanism.
Figure 10H:
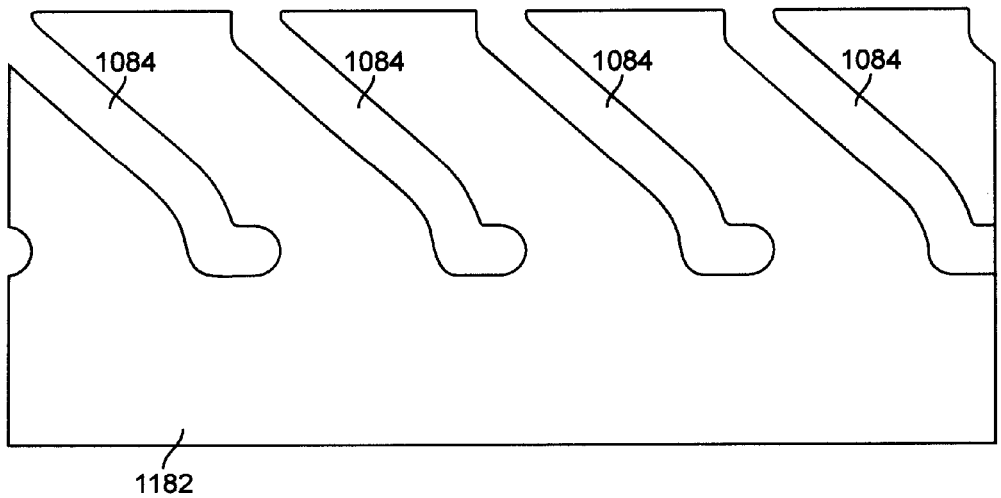

FIGS. 10G-10H illustrate another exemplary embodiment of a bayonet coupling. This embodiment is similar to the previous bayonet coupling in FIG. 10F, but instead of having two pins that mate with two slots, this embodiment has four pins that mate with four slots. FIG. 10G illustrates the male connector 1076 that is generally cylindrical and having four pins 1078 that extend radially outward from the body of the connector. The pins are preferably spaced 90 degrees apart, but this is not intended to be limiting. The female connector 1082 includes four slots 1084, preferably spaced 90 degrees apart. The slots receive the pins 1078 when the male connector is inserted into the female connector and rotated relative to one another. Other aspects of the male and female connector, and their operation generally take the same form as describe with respect to FIG. 10F above. FIG. 10H illustrates an exemplary method of forming the slotted female connector from a flat sheet. The slots 1084 may be machined (e.g. by EDM, photochemically etched, laser cut, etc.) into a flat sheet of material that is then rolled into a cylindrical shape to form the female connector. The female connector may also be cut from a tube. The male connector may be formed by press fitting, bonding, welding, etc. pins into the male connector or machined or molded.

Figure 11A:
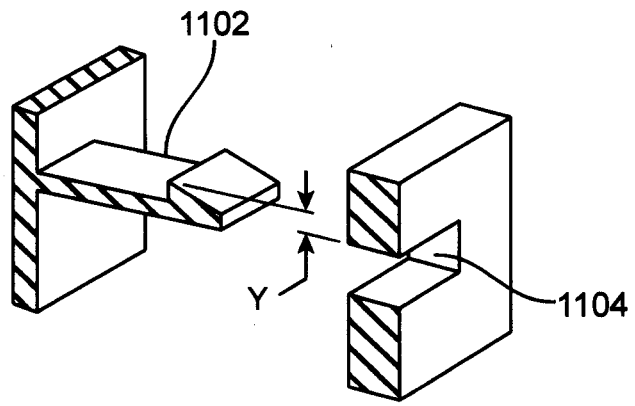
FIGS. 11A-11C illustrate exemplary embodiments of snap fits.
Figure 11B:
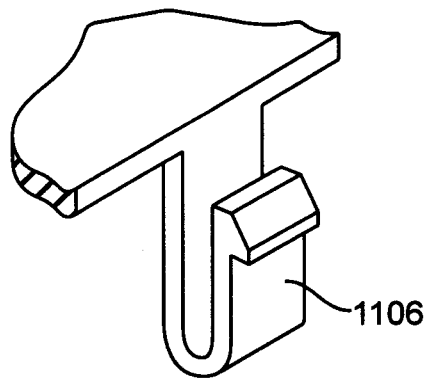
Figure 11C:
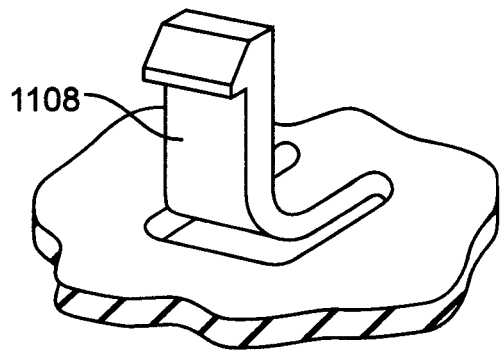

Other connectors include frangible connectors fabricated from breakable wires, strands, fibers, tubes, tabs, hooks, barbs, cantilevers, etc. that remain intact and connected until a certain force is applied, and the connector breaks. While these connectors are promising, they only allow the connection to be broken a single time, and reconnection is not possible. Therefore preferred embodiments may be connected and unconnected multiple times. FIGS. 11A-11C also illustrate snap fits which may be used as the connector mechanism. FIG. 11A illustrates a cantilevered snap fitting 1102 that locks with a recessed region 1104 in the mating part. FIG. 1106 illustrates a "U" shaped cantilevered snap fit 1106, and FIG. 11C illustrates an "L" shaped cantilevered snap fitting 1108. The cantilevered snap fitting may be a part of the shuttle sheath that mates with the recessed portion on one of the shafts, or the snap fitting may be on the shafts and the recessed portion may be a part of the shuttle sheath.

Figure 11D:
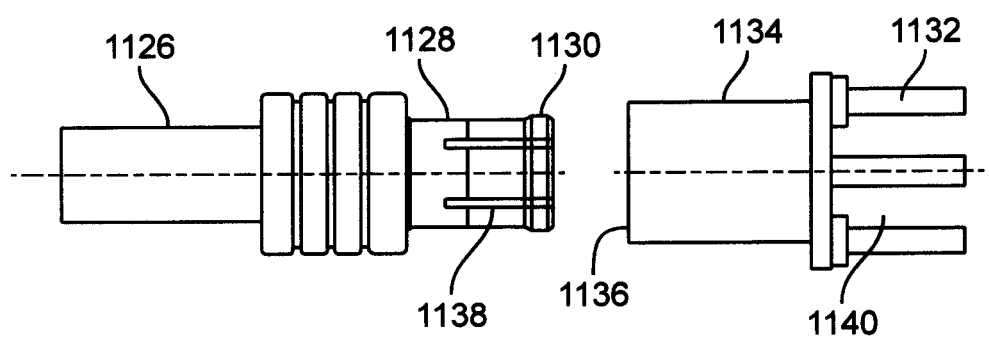
FIGS. 11D-11E illustrate still other embodiments of snap or press fit mechanisms.

FIG. 11D illustrates yet another embodiment of a snap fit that may be used to form the connector mechanisms described above. A connector includes a male portion 1126 and a female portion 1132. The male portion 1126 of the connector includes an elongate distal section 1128 having a raised annular flange 1130 near its distal end. A plurality of longitudinal slits 1138 form several resilient arms in the distal section 1128 that radially expand and contract. The female connector 1132 includes a proximal portion 1134 having a central channel 1136 therethrough. The central channel 1136 opens up into an enlarged region 1140. In use, the distal section 1128 is slidably inserted into the central channel 1136 forcing the resilient arms into a collapsed configuration. The male connector is advanced into the female connector until the annular flange 1130 enters the enlarged region 1140. The arms resiliently open back up to their unbiased configuration, forcing the annular flange outward, thereby releasably locking the male and female connectors together. The two may be pulled apart from one another upon application of adequate tensile force.

Figure 11E:
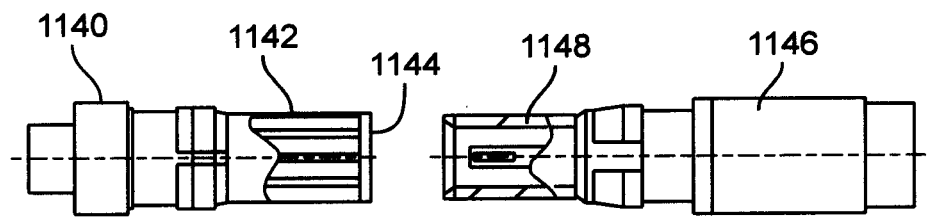

FIG. 11E illustrates a slide-on coupling mechanism which includes a male connector 1146 and a female connector 1140. The male connector has an elongate distal region 1148, and the female connector has a receiving portion 1142 with a central channel 1144 therethrough. The male and female connectors are pressed against one another such that the distal region 1148 is received in the receiving portion 1142. The size of the two connectors may be adjusted to provide an appropriate friction fit against one another to prevent unwanted release. The two connectors may be released from one another upon application of adequate tensile force.

Figure 12:
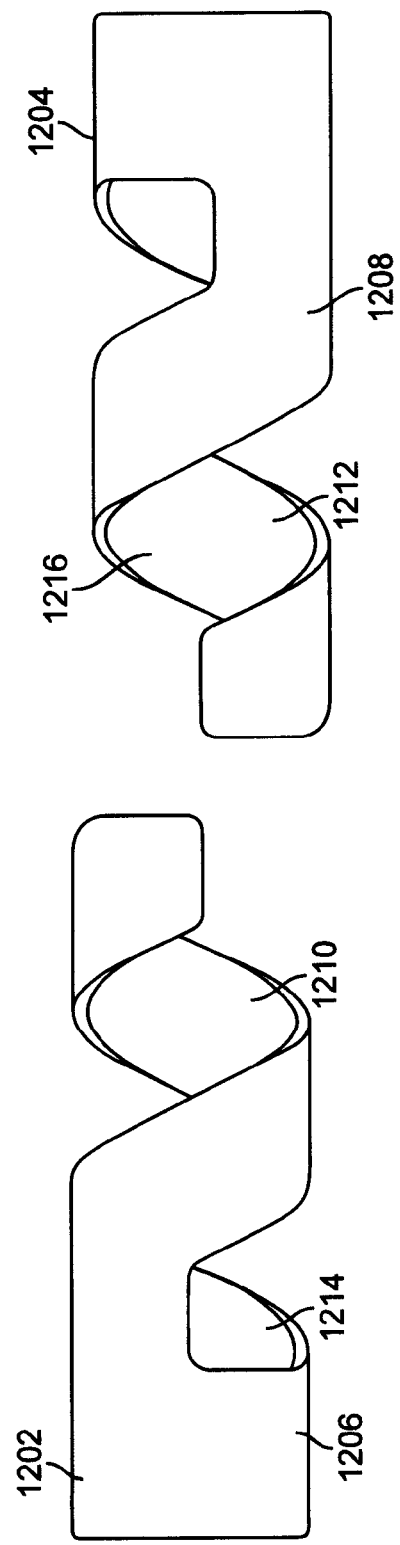
FIG. 12 illustrates yet another exemplary embodiment of a coupling mechanism.

FIG. 12 illustrates an exemplary embodiment of a spiral or helical coupling mechanism that may be used in any of the delivery catheter embodiments disclosed herein. The coupling mechanism includes a first spiral or helical connector 1202 and a second spiral or helical connector 1204. The first spiral connector includes a proximal portion 1206 that is preferably cylindrical and this may be joined by bonding, welding, threading, press fitting, etc. to either end of the shuttle sheath, or the inner shaft or outer shaft. A distal portion 1210 of the spiral connector winds in a spiral or helical pattern in a first direction to form a thread-like region. The outer diameter of the spiral connector is preferably constant along the entire length of the connector, but this is not intended to be limiting. Additionally, a central channel 1214 extends through spiral connector 1202, and the inner diameter of the first connector 1202 is also preferably constant along the connector, but not required. The second spiral connector 1204 is identical to the first connector 1202, rotated 180 degrees. The second connector 1204 includes a proximal portion 1208 that is also preferably cylindrical for joining with the shuttle sheath, inner shaft, or outer shaft by one of the methods listed above, or known to those of skill in the art. A distal portion 1208 of the second connector 1204 winds in a spiral or helical pattern in a second direction opposite the first direction to form a thread-like region. The outer diameter of the spiral connector 1204 is preferably constant along its entire length, but this is not meant to be limiting. Also, a central channel 1212 extends through the spiral connector 1204, and the inner diameter of second connector 1204 is also preferably constant along its length, but not required. The two connectors may be joined together by rotating one connector relative to the other connector so that the thread-like regions overlap and engage with one another. Also, similar to other threaded-type embodiments disclosed herein, when two spiral connectors are used on opposite ends of the shuttle sheath, rotation in one direction will couple the shuttle sheath to one of the shafts (inner or outer shaft) while decoupling the shuttle sheath from the other shaft. Similarly, rotation in the opposite direction will decouple the shuttle sheath at one end and couple it at the opposite end. The pitch of the helix is preferably set so that rotation is smooth with relatively low friction and so that the number of turns required to lock the two connectors together is comfortable to most operators. One advantage of this design is that both connectors may be cut from a single piece of tubing having a length less than the combined length of the individual connectors. Additionally, only a single connector need be manufactured since both halves are mirror images of one another. One connector may be used on one end of the shuttle sheath or shaft, while the same part may be flipped over and used on the opposite end. This is desirable since it helps reduce component inventory and ensures ease of manufacturing.

Figure 6A:
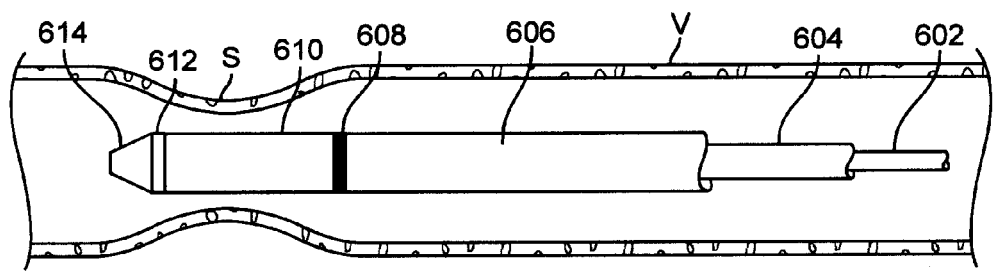
FIGS. 6A-6C illustrate an exemplary method of stenting a vessel with distal stent release.
Figure 6B:
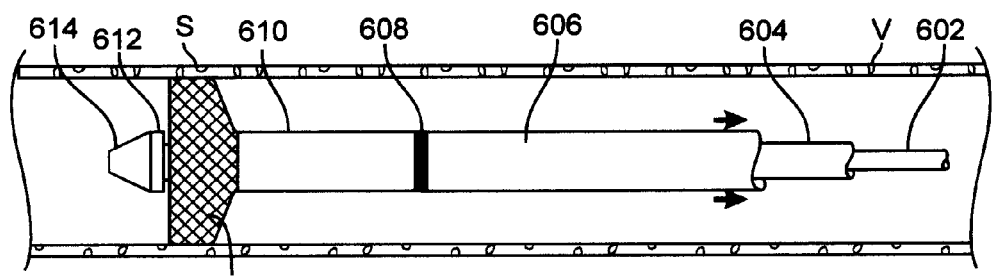
Figure 6C:
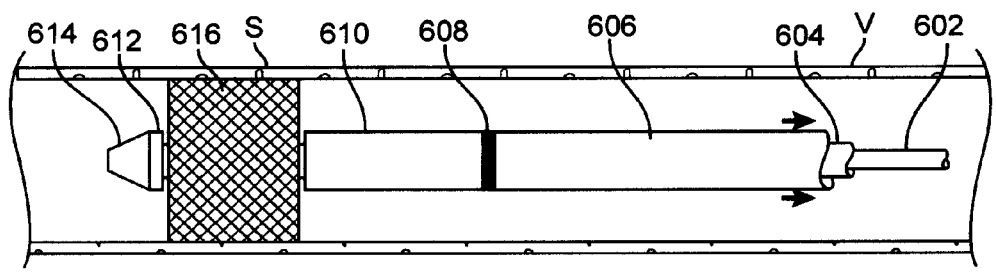

FIGS. 6A-6C illustrate an exemplary method of treating a vessel with a bi-directional stent delivery system such as those described above. In FIG. 6A, the delivery catheter is advanced to a target treatment site in a vessel V. In this embodiment the treatment site is a stenotic region S of a vein caused by compression from surrounding vessels, bone, or other anatomical structures. The delivery catheter includes an inner shaft 602, middle shaft 604, outer shaft 606, shuttle sheath 610, and proximal lock 608, distal lock 612, and nose cone 614. Other aspects of the catheter such as the proximal hubs on the shafts have been omitted for clarity. The proximal lock 608 is shown in the locked position (shown with darkened rectangle), while the distal lock is shown in the unlocked configuration (shown by the white rectangle). Once the catheter is advanced to the target treatment site, the outer sheath is proximally retracted which also proximally retracts the shuttle sheath 610. The stent 616 is then permitted to self expand in the proximal direction, as seen in FIG. 6B until is fully expands into its radially expanded configuration which engages the vessel walls and alleviates the stenosis caused by the compression, as seen in FIG. 6C. The delivery catheter is then removed from the patient. In this exemplary method, as well as others described herein, the delivery catheter may be introduced percutaneously into the vessel and advanced transluminally over a guidewire, such as an 0.035" guidewire. Alternatively, the catheter may be introduced via a surgical cutdown.

Figure 7A:
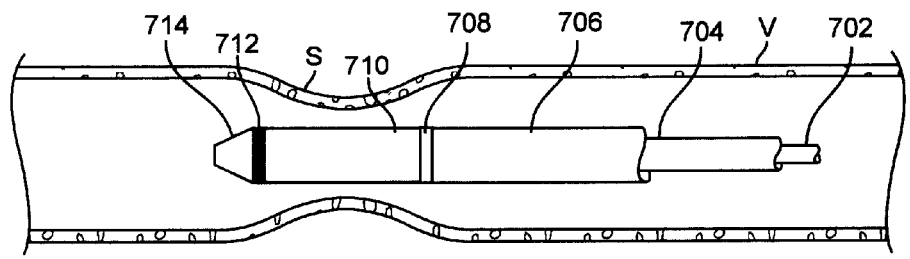
FIGS. 7A-7C illustrate an exemplary method of stenting a vessel with proximal stent release.
Figure 7B:
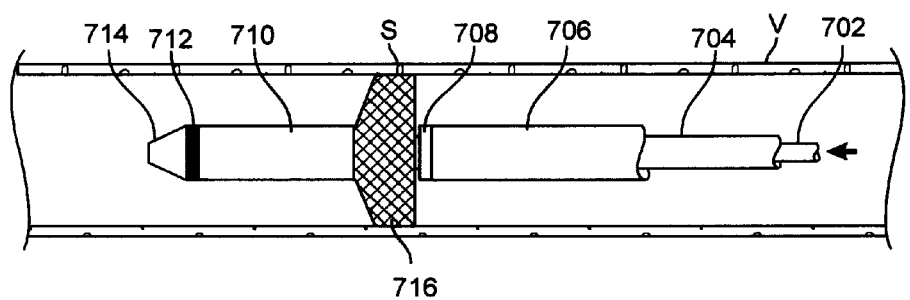
Figure 7C:
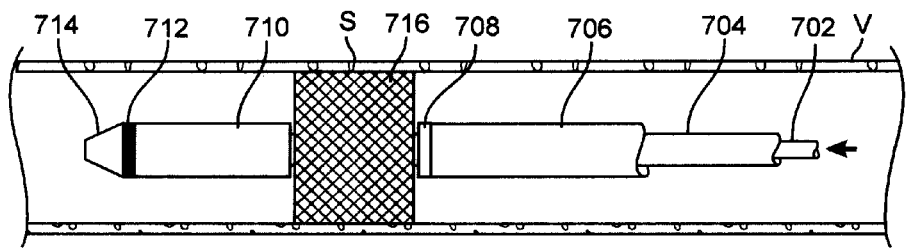

FIGS. 7A-7C illustrate another exemplary method of treating a vessel with the bi-directional stent delivery system such as those previously described above. In FIG. 7A the delivery catheter is advanced to a target treatment site in a vessel V. In this embodiment the treatment site is a stenotic region S of a vein caused by compression from surrounding vessels, bone, or other anatomical structures. The delivery catheter includes an inner shaft 702, middle shaft 704, outer shaft 706, shuttle sheath 710, proximal lock 708, distal lock 712, and nose cone 614. Other aspects of the delivery catheter, such as the proximal hubs have been omitted for clarity. The proximal lock 708 is shown in the unlocked configuration (shown by the white rectangle), while the distal lock 712 is shown in the locked configuration (shown by the darkened rectangle). Once the catheter is advanced to the target treatment site, the inner shaft is advanced distally, thereby also advancing the shuttle sheath 710. The stent 716 becomes unconstrained and self expands in the distal direction, as seen in FIG. 7B until it fully expands into its radially expanded configuration which engages the vessel walls and alleviates the stenosis caused by the compression, as illustrated in FIG. 7C. The delivery catheter is then removed from the patient.

Figure 8A:
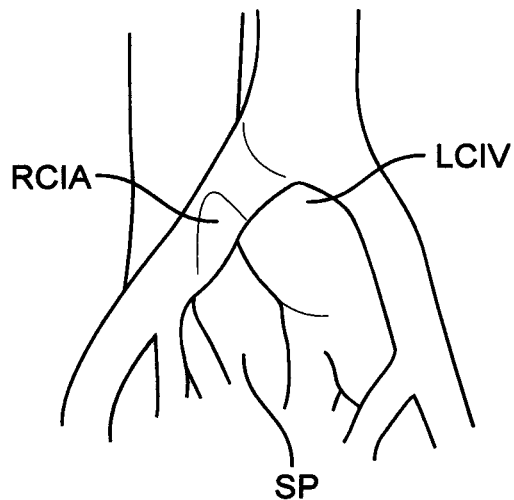
FIGS. 8A-8B illustrate the basic anatomy of iliac vein compression syndrome.
Figure 8B:
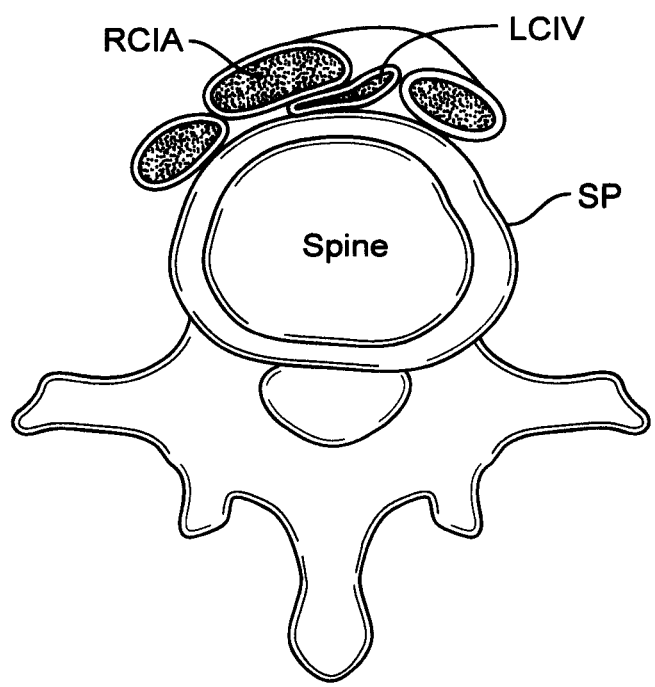

FIGS. 8A-8B illustrate exemplary stenting of a vein as a treatment for venous stenosis. Venous stenosis may be caused by clotting, scarring following blood clots or by focal external compressive forces on a venous vessel (such as in the femoral vein where it crosses the inguinal ligament or in the pelvic vein where it is crossed by overlaying pelvic arteries). The stent or stents may be delivered to the vein using any of the embodiments described above. FIGS. 8A-8B illustrate a vein experiencing external compressive forces. In FIG. 8A the right common iliac artery RCIA is nested against the left common iliac vein LCIV. The spine SP is posterior to both vessels RCIA, LCIV, therefore the left common iliac vein LCIV may be pinched in between a portion of the right common iliac artery RCIV and the spine SP. FIG. 8B illustrates a cross section of FIG. 8A and highlights the pinched portion of the left common iliac vein LCIV. Pinching of the vein obstructs venous outflow. Venous outflow obstruction of the iliac vein, the common outflow tract of the lower limb, can result in severe clinical symptoms. Obstruction of the iliac veins can be attributed to thrombus formation or from external compression from the overlying arterial tree, with possible additional pressure extending from the spine. Venous outflow obstruction is a clinically relevant contributor to chronic venous disease. When combined with venous reflux, outflow obstruction can lead to venous hypertension and the most severe symptoms associated with advanced venous disease such as swelling, discoloration, claudication and ulceration.

Treatment has traditionally been by surgical bypass. However, in the past decade, percutaneous endovenous stenting has emerged as the method of choice in treating venous outflow obstruction due to chronic venous disease. However, there are currently no FDA approved stents or delivery systems for this treatment, and therefore such use is considered off label use. The placement of stents has also proven useful to relieve obstruction that has been revealed after removal of acute iliofemoral thrombus, after a DVT or from obstruction that has been caused by malignant tumors or retroperitoneal thrombosis.

Figure 9:
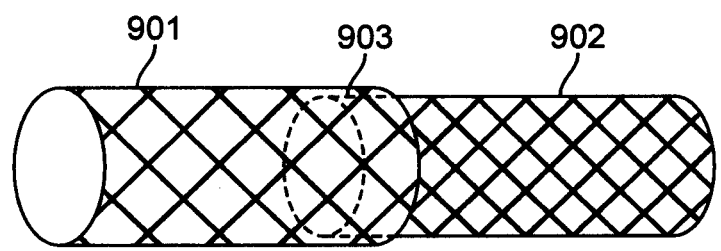
FIG. 9 illustrates overlapping of two or more stents.

Stenting of the vein alleviates the pinch point, thereby permitting normal venous outflow. One or more stents may be placed in the vein. In cases where multiple stents are deployed, the stents may be placed end-to-end, or the stents may be overlapped with one another. FIG. 9 illustrates how two stents 901, 902 may have a region 903 where the two stents overlap with one another. In this embodiment, stent 902 is radially expanded such that a portion of the stent expands into the other stent 901. Overlapping of stents is discussed in greater detail in U.S. patent application Ser. No. 12/903,056, previously incorporated by reference. The stents in this embodiment or those described elsewhere in this specification may also include a therapeutic agent such as an antithrombogenic such as heparin, a thrombolytic agent, or another therapeutic agent for reducing blood clots or for another therapy.

In any of the exemplary methods described herein, after the stent or stents have been deployed in the vessel or target treatment site, they may be post-dilated using a balloon catheter in order to tack the stents into the tissue and maximize their expanded diameter. This may be performed with a separate balloon dilatation catheter, or a balloon or other expandable member may be included with embodiments of the delivery system disclosed herein. Positioning and expansion of stents may be verified using intravascular ultrasound (IVUS). The IVUS catheter may be a separate catheter or it may be integrated into the present delivery system. In some embodiments, the IVUS probe is integrated into a standard guidewire, such as an 0.035" guidewire, therefore a conventional guidewire is replaced by the IVUS guidewire.

Although the exemplary embodiments have been described in some detail for clarity of understanding and by way of example, a variety of additional modifications, adaptations and changes may be clear to those of skill in the art. One of skill in the art will appreciate that the various features described herein may be combined with one another or substituted with one another. Hence, the scope of the present invention is limited solely by the appended claims.

What is claimed is:

1. A bi-directional method for deploying a prosthesis at a treatment site in a patient, said method comprising:
providing a delivery catheter comprising a prosthesis having a proximal end and a distal end, the prosthesis in a collapsed configuration and disposed on the delivery catheter, wherein the delivery catheter comprises an inner elongate shaft, an outer elongate shaft and a shuttle sheath disposed over the prosthesis;
delivering the prosthesis to the target treatment site;
selecting a deployment direction for the prosthesis, wherein the deployment direction comprises radially expanding the prosthesis from the proximal end thereof to the distal end thereof, or radially expanding the prosthesis from the distal end thereof to the proximal end thereof, wherein selecting one deployment direction for the prosthesis comprises:
coupling the inner elongate shaft with the shuttle sheath;
decoupling the outer elongate shaft from the shuttle sheath;
distally advancing the inner elongate shaft distally thereby advancing the shuttle sheath distally away from the prosthesis; and
radially expanding the prosthesis from the proximal end thereof to the distal end thereof;
removing a constraint from the prosthesis thereby permitting the prosthesis to radially expand in the selected deployment direction;
radially expanding the prosthesis from the collapsed configuration to an expanded configuration in the selected deployment direction so that the expanded prosthesis engages tissue at the target treatment site; and
withdrawing the delivery catheter from the patient and leaving the prosthesis deployed at the target treatment site.

2. The method of claim 1, wherein the prosthesis comprises a first stent.

3. The method of claim 1, wherein the prosthesis comprises a first stent and a second stent unattached and axially separated from the first stent by a gap.

4. The method of claim 1, wherein delivering the prosthesis comprises advancing the delivery catheter through vasculature of the patient to the target treatment site.

5. The method of claim 1, wherein the delivery catheter has a proximal end, a distal end, and a lumen therebetween, and delivering the prosthesis comprises slidably advancing the delivery catheter over a guidewire disposed in the lumen.

6. The method of claim 1, wherein delivering the prosthesis comprises positioning the prosthesis in a vein.

7. The method of claim 6, wherein the vein comprises the iliac vein.

8. The method of claim 1, wherein coupling the inner elongate shaft with the shuttle sheath comprises threadably engaging the inner elongate shaft with the shuttle sheath.

9. The method of claim 1, wherein coupling the inner elongate shaft with the shuttle sheath comprises helically engaging the inner elongate shaft with the shuttle sheath.

10. The method of claim 1, wherein coupling comprises coupling the inner elongate shaft and the shuttle sheath with a bayonet coupling.

11. The method of claim 1, wherein decoupling the outer elongate shaft from the shuttle sheath comprise threadably disengaging the outer elongate shaft from the shuttle sheath.

12. The method of claim 1, wherein decoupling the outer elongate shaft from the shuttle sheath comprise helically disengaging the outer elongate shaft from the shuttle sheath.

13. The method of claim 1, wherein decoupling comprises releasing a bayonet coupling between the outer elongate shaft and the shuttle sheath.

14. The method of claim 1, wherein selecting another deployment direction for the prosthesis comprises:
coupling the outer elongate shaft with the shuttle sheath;
proximally retracting the outer elongate shaft thereby retracting the shuttle sheath proximally away from the prosthesis; and
radially expanding the prosthesis from the distal end thereof to the proximal end thereof.

15. The method of claim 14, wherein coupling the outer elongate shaft with the shuttle sheath comprises threadably engaging the outer elongate shaft with the shuttle sheath.

16. The method of claim 14, wherein coupling the outer elongate shaft with the shuttle sheath comprises helically engaging the outer elongate shaft with the shuttle sheath.

17. The method of claim 14, wherein coupling comprises coupling the outer elongate shaft and the shuttle sheath with a bayonet coupling.

18. The method of claim 14, wherein selecting another deployment direction further comprises:
decoupling the inner elongate shaft from the shuttle sheath.

19. The method of claim 18, wherein decoupling the inner elongate shaft from the shuttle sheath comprises threadably decoupling the inner elongate shaft from the shuttle sheath.

20. The method of claim 18, wherein decoupling the inner elongate shaft from the shuttle sheath comprises helically decoupling the inner elongate shaft from the shuttle sheath.

21. The method of claim 18, wherein decoupling comprises releasing a bayonet coupling between the inner elongate shaft and the shuttle sheath.

22. The method of claim 14, wherein removing the constraint comprises proximally retracting the shuttle sheath away from the prosthesis so that the prosthesis is unconstrained from radial expansion in a direction extending from the distal end of the prosthesis to the proximal end of the prosthesis.

23. The method of claim 1, wherein removing the constraint comprises distally advancing the shuttle sheath away from the prosthesis so that the prosthesis is unconstrained from radial expansion in a direction extending from the proximal end of the prosthesis to the distal end of the prosthesis.

24. The method of claim 1, wherein radially expanding the prosthesis comprises self-expanding a stent.

25. The method of claim 1, wherein withdrawing the delivery catheter from the patient comprises withdrawing the delivery catheter from the patient's vasculature.

26. The method of claim 1, wherein the prosthesis comprises two prostheses, and selecting the deployment direction for the two prostheses comprises:
selecting a first deployment direction for the first prosthesis;
radially expanding the first prosthesis in the first deployment direction; and
radially expanding the second prosthesis in a second deployment direction opposite of the first deployment direction.

27. The method of claim 1, further comprising visualizing the expanded prosthesis.

28. The method of claim 27, wherein visualizing comprises observing the expanded prosthesis with ultrasound or fluoroscopy.

29. The method of claim 27, further comprising retracting the radially expanded prosthesis into a shuttle sheath;
repositioning the prosthesis; and
radially expanding the prosthesis.

30. The method of claim 1, further comprising dilating the radially expanded prosthesis with an expandable member.

31. A method for deploying a prosthesis at a treatment site in a patient, said method comprising:
providing a delivery catheter comprising a prosthesis having a proximal end and a distal end, the prosthesis in a collapsed configuration and disposed on the delivery catheter, and an outer shaft of the delivery catheter being uncoupled from a shuttle sheath disposed over the prosthesis;
delivering the prosthesis to the target treatment site;
deploying the prosthesis by radially expanding the prosthesis from the proximal end thereof to the distal end thereof by distally advancing an inner shaft to advance distally, the shuttle sheath disposed over the prosthesis, to thereby remove a constraint from the prosthesis and allow the prosthesis to radially expand from the proximal end to the distal end; and
withdrawing the delivery catheter from the patient and leaving the prosthesis deployed at the target treatment site.

* * * * *